(12) United States Patent
Chandrasekher et al.

(10) Patent No.: US 7,855,269 B2
(45) Date of Patent: Dec. 21, 2010

(54) METHOD FOR TREATING INFLAMMATION

(75) Inventors: Yasmin A. Chandrasekher, Mercer Island, WA (US); Stephen R. Jaspers, Edmonds, WA (US)

(73) Assignee: ZymoGenetics, Inc., Seattle, WA (US)

( * ) Notice: Subject to any disclaimer, the term of this patent is extended or adjusted under 35 U.S.C. 154(b) by 1142 days.

(21) Appl. No.: 09/951,268

(22) Filed: Sep. 13, 2001

(65) Prior Publication Data

US 2002/0085992 A1 Jul. 4, 2002

Related U.S. Application Data

(60) Provisional application No. 60/233,305, filed on Sep. 15, 2000.

(51) Int. Cl.
*C07K 14/00* (2006.01)
(52) U.S. Cl. ..................................................... 530/350
(58) Field of Classification Search ....................... None
See application file for complete search history.

(56) References Cited

U.S. PATENT DOCUMENTS

| | | | | |
|---|---|---|---|---|
| 5,723,299 | A | 3/1998 | Bell et al. | 435/7.1 |
| 5,789,192 | A | 8/1998 | Moore et al. | 435/69.1 |
| 5,843,725 | A | 12/1998 | Sledziewski et al. | 435/69.7 |
| 5,945,511 | A | 8/1999 | Lok et al. | 530/350 |
| 5,985,614 | A | 11/1999 | Rosen et al. | 435/69.52 |
| 6,020,163 | A | 2/2000 | Conklin | 435/69.1 |
| 6,486,301 | B1 | 11/2002 | Ebner et al. | 530/351 |
| 6,576,743 | B1 | 6/2003 | Conklin et al. | 530/351 |
| 6,610,286 | B2 | 8/2003 | Thompson et al. | 424/85.2 |
| 2002/0042366 | A1 | 4/2002 | Thompson et al. | 514/12 |

FOREIGN PATENT DOCUMENTS

| | | |
|---|---|---|
| WO | WO94/013801 | 6/1994 |
| WO | WO99/003982 | 1/1999 |
| WO | WO99/007740 | 2/1999 |
| WO | WO99/007848 | 2/1999 |
| WO | WO99/027103 | 6/1999 |
| WO | WO99/037772 | 7/1999 |
| WO | WO99/046281 | 9/1999 |
| WO | WO99/046379 | 9/1999 |
| WO | WO99/061630 | 12/1999 |
| WO | WO00/012708 | 3/2000 |
| WO | WO00/039161 | 7/2000 |
| WO | WO 00/042189 | 7/2000 |
| WO | WO 00/073457 | 12/2000 |
| WO | WO 00/078961 | 12/2000 |
| WO | WO 01/012672 | 2/2001 |
| WO | WO01/46232 | 6/2001 |
| WO | WO 01/046261 | 6/2001 |
| WO | WO 02/012345 | 2/2002 |
| WO | WO 02/058724 | 8/2002 |
| WO | WO 02/070001 | 9/2002 |
| WO | WO 02/072607 | 9/2002 |
| WO | WO 03/039444 | 5/2003 |
| WO | WO 03/051384 | 6/2003 |
| WO | WO2004/085475 | 10/2004 |

OTHER PUBLICATIONS

Abbas et al., "Cellular and Molecular Immunology",4th Ed., pp. 519-520, W.B. Saunders Company, 2000.
Albert et al., "Molecular Biology of the Cell," 3rd Ed., pp. 156-159, Garland Publishing, Inc., 1994.
Asadullah et al., *Arch Dermatol* 138:1189-1196, 2002.
Asadullah et al., *Pharmacol Rev.* 55(2):241-269, 2003.
Blumberg et al., *Cell* 104:9-19, 2001.
Cameron et al., "Cytokines and Chemokines in Autoimmune Disease," pp. 8-32, Eurekah.com and Klawer Academic/Plenum Publishers, 2003.
Conti et al., *Immunology Letters* 88:171-174, 2003.
Cunningham et al., *Science* 244:1081-1085, 1989.
Davis et al., *Cell* 87:1161-1169, 1996.
De Groot-Kruseman et al., *J. Interferon & Cytokine Research* 22(Suppl. 1):S-97, Abstract P-2-1, 2002.
Dumoutier et al., *Eur. Cytokin Netw* 13(2):5-15, 2002.
Dumoutier et al., *J. Immunol.* 167:3545-3549, 2001.
Dynan et al., *Nature* 316:774-778; 1985.
Fickenscher et al., *TRENDS in Immunology* 23(2):89-96,.2002.
George et al., "Macromolecular Sequencing & Synthesis," pp. 127-149, Ch. 12, Alan R. Liss, Inc., 1988.
Gröne, *Veterinary Immunol. and Immunopathol.* 88:1-12, 2002.
Harlow et al., "Antibodies a Laboratory Manual," p. 76, Ch. 5, Cold Springs Harbor Laboratory, 1988.
He et al., *J. Interferon & Cytokine Research* 22(Suppl. 1):S-97, Abstract P-1-23, 2002.
Henikoff et al., *Proc. Nat. Acad. Sci.* USA 89:10915-10919, 1992.
Hosoi et al., *The 75th Annual Meeting, Department of Pharmacology Kumamoto University* , p. 89P, Abstract P-112, 2002.
Kotenko, *Cytokine & Growth Factor Reviews* 13:223-240, 2002.
Kotenko et al., *J. Biol. Chem.* 276(4):2725-2732, 2001.
Kotenko et al., *Oncogene* 19:2557-2565, 2000.
Kunz et al., *J. Interferon & Cytokine Research* 22(Suppl. 1):S-97-S-98, Abstract P-2-3, 2002.
Last et al., *J. Investigative Dermatology* 119(1):325, Abstract 707, 2002.
Liu et al., *Blood* 100(11):189a-190a, Abstract #710, 2002.
Liu et al., *Journal of Immunology* 152:1821-1829, 1994.
Liu et al., *Blood* 102(9):3206-3209, 2003.

(Continued)

*Primary Examiner*—Michael Pak
(74) *Attorney, Agent, or Firm*—Paul G. Lunn; Shelby J. Walker; Nicholas V. Sherbina

(57) ABSTRACT

A method for treating down-regulating IL-19 or mda7 by administering the soluble IL-20RA/IL-20R heterodimeric receptor.

1 Claim, No Drawings

OTHER PUBLICATIONS

Lutfalla et al., *Genomics* 16:366-373, 1993.
Lutfalla et al., *J. Mol. Evolution* 41:338-344, 1995.
Lillehoj et al., "Antibody Techniques," pp. 291-305, Ch. 13, Academic Press, Inc., 1994.
McKinnon et al., *Drug News and Perspectives* 9(7):389-398, 1996.
Merck Manual 17th Ed., pp. 920-925, 1999.
Mohler et al., *FASB J. US Fed of American Soc. For Experimental Biology* 6(4):A1123, 1992.
Musso et al., *J. Interferon & Cytokine Research* 22(Suppl. 1):S-98, Abstract P-2-4, 2002.
Ozaki et al., *J. Biol. Chem.* 277(33):29355-29358, 2002.
Parrish-Novak et al., *J. Biol. Chem.* 277(49):47517-47523, 2002.
Parrish-Novak et al, *J. Interferon & Cytokine Research* 22(Suppl. 1):S-46, Abstract W-1-5, 2002.
Pirhonen et al., *J. Interferon & Cytokine Research* 22(Suppl. 1): S-98, Abstract P-2-6, 2002.
Ramesh et. al., *Cancer Gene Therapy:* S3, Abstract 008, 2002.
Rich et al., *Curr Biol.* 11(13):R531-R534, 2001.
Rich, *Expert Opin. Ther. Targets* 7(2):165-174, 2003.
Rohovsky et al., "Growth Factors and Wound Healing" pp. 8-26, Ch. 2, Springer, 1997.
Roitt et al., "Immunology," 4th Ed., pp. 28.10-28.12, Mosby, 1996.
Rose-John, *Acta Biochimica Polonica* 50(3):603-611, 2003.
Salazar et al., *Eur. J. of Clin. Invest.* 31(12):1070-1077, 2001.
Slavin, *J. Immunol. Immunopharmacol* 17(1):25-29, 1997.
Stolina et al., *J. Interferon & Cytokine Research* 22(Suppl.1):S-98-S-99, Abstract P-2-7, 2002.
Strengell et al., *J. Interferon & Cytokine Research* 22(Suppl. 1):S-99, Abstract P-2-8, 2002.
Tachiiri et al., *Genes and Immunity* 4:153-159, 2003.
Vandenbroeck et al., *J. Biol. Chem.* 277(28):25668-25676, 2002.
Volk et al., *TRENDS in Immunology* 22(8):414-417, 2001.
Walter, *Immunologic Res.* 26(1-3):303-308, 2002.
Whitters et al., *J. Interferon & Cytokine Research* 22(Suppl. 1):S-99-S-100, Abstract P-2-11, 2002.
Witek et al. *J. Interferon & Cytokine Research* 22(Suppl. 1):S-100, Abstract P-2-12, 2002.
Wolk et al., *J. Immunol.* 168:5397-5402, 2002.
Wuyts et al., *Eur J. Biochem.* 260:421-429, 1999.
Xie et al., *J. Biol. Chem.* 275(40):31335-31339, 2000.
Xu et al., *Proc. Nat. Acad. Sci.* USA. 98(17):9511-9516, 2001.
EST from Incyte Pharmaceuticals Inc., INC1429789, 1996.
EST from Incyte Pharmaceuticals Inc., INC1922140, 1996.
EST from Incyte Pharmaceuticals Inc., INC1923851, 1996.
EST from Incyte Pharmaceuticals Inc., INC2119350, 1996.
EST from Incyte Pharmaceuticals Inc., INC2270605, 1996.
EST from Incyte Pharmaceuticals Inc., INC2699058, 1997.
EST from Incyte Pharmaceuticals Inc., INC2701079, 1997.
EST from Incyte Pharmaceuticals Inc., INC2720417, 1997.
EST from Incyte Pharmaceuticals Inc., INC2763478, 1997.
EST from Incyte Pharmaceuticals Inc., INC3256488, 1997.
EST from Incyte Pharmaceuticals Inc., INC3257185, 1997.
EST from Incyte Pharmaceuticals Inc., INC3316826, 1997.
EST from Incyte Pharmaceuticals Inc., INC3376533, 1997.
EST from Incyte Pharmaceuticals Inc., INC357666, 1995.
EST from Incyte Pharmaceuticals Inc., INC4304592, 1998.
EST from Incyte Pharmaceuticals Inc., INC758088, 1996.
EST from Incyte Pharmaceuticals Inc., INC819592, 1996.
EST from Incyte Pharmaceuticals Inc., INC904360, 1996.
EST from TIGR Tentative Human Consensus, THC174656, 1997.
EST from TIGR Tentative Human Consensus, THC197949, 1997.
EST from TIGR Tentative Human Consensus, THC215509, 1997.
GenBank Accession No. AA018585, 1995.
GenBank Accession No. AA018749, 1995.
GenBank Accession No. AA035594, 1995.
GenBank Accession No. AA132964, 1995.
GenBank Accession No. AA134881, 1995.
GenBank Accession No. AA135185, 1995.
GenBank Accession No. AA135300, 1995.
GenBank Accession No. AA299011, 1995.
GenBank Accession No. AA412292, 1997.
GenBank Accession No. AA470014, 1997.
GenBank Accession No. AA494556, 1997.
GenBank Accession No. AA514541, 1997.
GenBank Accession No. AA516435, 1997.
GenBank Accession No. AA528216, 1997.
GenBank Accession No. AA583432, 1997.
GenBank Accession No. AA632915, 1997.
GenBank Accession No. H17201, 1995.
GenBank Accession No. H17978, 1995.
GenBank Accession No. N62509, 1995.
GenBank Accession No. N79409; 1995.
GenBank Accession No. R14678, 1995.
GenBank Accession No. R42401, 1995.
GenBank Accession No. T70354, 1995.
GenBank Accession No. T70439, 1995.

SEQUENCE LISTING

```
<160> NUMBER OF SEQ ID NOS: 42

<210> SEQ ID NO 1
<211> LENGTH: 3516
<212> TYPE: DNA
<213> ORGANISM: Homo sapiens
<220> FEATURE:
<221> NAME/KEY: CDS
<222> LOCATION: (237)...(1895)

<400> SEQUENCE: 1
```

-continued

```
tccagctggg tagccggggg agcgcgcgtg ggggctccgc gagtcgctcg cccttggttt      60
ctggggaagc ctgggggacg cggctgtggc ggaggcgccc tgggactcag gtcgcctgga     120
gcgtggcacg cagagcccca ggcgcggagc tgaggccgcg cggccgcgct tggccccagc     180
gggcgtggga ctgagcagtc tgctgccccc cgacatgtga cccagccccg ccgccc atg    239
                                                                Met
                                                                1
```

| cgg<br>Arg | gct<br>Ala | ccc<br>Pro | ggc<br>Gly<br>5 | cgc<br>Arg | ccg<br>Pro | gcc<br>Ala | ctg<br>Leu | cgg<br>Arg<br>10 | ccg<br>Pro | ctg<br>Leu | ccg<br>Pro | ctg<br>Leu | ccg<br>Pro<br>15 | ccg<br>Pro | ctg<br>Leu | 287 |
| --- | --- | --- | --- | --- | --- | --- | --- | --- | --- | --- | --- | --- | --- | --- | --- | --- |
| ctg<br>Leu | ctg<br>Leu | ttg<br>Leu<br>20 | ctc<br>Leu | ctg<br>Leu | gcg<br>Ala | gcg<br>Ala | cct<br>Pro<br>25 | tgg<br>Trp | gga<br>Gly | cgg<br>Arg | gca<br>Ala | gtt<br>Val<br>30 | ccc<br>Pro | tgt<br>Cys | gtc<br>Val | 335 |
| tct<br>Ser | ggt<br>Gly<br>35 | ggt<br>Gly | ttg<br>Leu | cct<br>Pro | aaa<br>Lys | cct<br>Pro<br>40 | gca<br>Ala | aac<br>Asn | atc<br>Ile | acc<br>Thr | ttc<br>Phe<br>45 | tta<br>Leu | tcc<br>Ser | atc<br>Ile | aac<br>Asn | 383 |
| atg<br>Met<br>50 | aag<br>Lys | aat<br>Asn | gtc<br>Val | cta<br>Leu | caa<br>Gln<br>55 | tgg<br>Trp | act<br>Thr | cca<br>Pro | cca<br>Pro | gag<br>Glu<br>60 | ggt<br>Gly | ctt<br>Leu | caa<br>Gln | gga<br>Gly | gtt<br>Val<br>65 | 431 |
| aaa<br>Lys | gtt<br>Val | act<br>Thr | tac<br>Tyr | act<br>Thr<br>70 | gtg<br>Val | cag<br>Gln | tat<br>Tyr | ttc<br>Phe | ata<br>Ile<br>75 | tat<br>Tyr | ggg<br>Gly | caa<br>Gln | aag<br>Lys | aaa<br>Lys<br>80 | tgg<br>Trp | 479 |
| ctg<br>Leu | aat<br>Asn | aaa<br>Lys | tca<br>Ser<br>85 | gaa<br>Glu | tgc<br>Cys | aga<br>Arg | aat<br>Asn | atc<br>Ile<br>90 | aat<br>Asn | aga<br>Arg | acc<br>Thr | tac<br>Tyr | tgt<br>Cys<br>95 | gat<br>Asp | ctt<br>Leu | 527 |
| tct<br>Ser | gct<br>Ala | gaa<br>Glu<br>100 | act<br>Thr | tct<br>Ser | gac<br>Asp | tac<br>Tyr | gaa<br>Glu<br>105 | cac<br>His | cag<br>Gln | tat<br>Tyr | tat<br>Tyr | gcc<br>Ala<br>110 | aaa<br>Lys | gtt<br>Val | aag<br>Lys | 575 |
| gcc<br>Ala | att<br>Ile<br>115 | tgg<br>Trp | gga<br>Gly | aca<br>Thr | aag<br>Lys | tgt<br>Cys<br>120 | tcc<br>Ser | aaa<br>Lys | tgg<br>Trp | gct<br>Ala | gaa<br>Glu<br>125 | agt<br>Ser | gga<br>Gly | cgg<br>Arg | ttc<br>Phe | 623 |
| tat<br>Tyr<br>130 | cct<br>Pro | ttt<br>Phe | tta<br>Leu | gaa<br>Glu | aca<br>Thr<br>135 | caa<br>Gln | att<br>Ile | ggc<br>Gly | cca<br>Pro | cca<br>Pro<br>140 | gag<br>Glu | gtg<br>Val | gca<br>Ala | ctg<br>Leu | act<br>Thr<br>145 | 671 |
| aca<br>Thr | gat<br>Asp | gag<br>Glu | aag<br>Lys | tcc<br>Ser<br>150 | att<br>Ile | tct<br>Ser | gtt<br>Val | gtc<br>Val | ctg<br>Leu<br>155 | aca<br>Thr | gct<br>Ala | cca<br>Pro | gag<br>Glu | aag<br>Lys<br>160 | tgg<br>Trp | 719 |
| aag<br>Lys | aga<br>Arg | aat<br>Asn | cca<br>Pro<br>165 | gaa<br>Glu | gac<br>Asp | ctt<br>Leu | cct<br>Pro | gtt<br>Val<br>170 | tcc<br>Ser | atg<br>Met | caa<br>Gln | caa<br>Gln | ata<br>Ile<br>175 | tac<br>Tyr | tcc<br>Ser | 767 |
| aat<br>Asn | ctg<br>Leu | aag<br>Lys<br>180 | tat<br>Tyr | aac<br>Asn | gtg<br>Val | tct<br>Ser | gtg<br>Val<br>185 | ttg<br>Leu | aat<br>Asn | act<br>Thr | aaa<br>Lys | tca<br>Ser<br>190 | aac<br>Asn | aga<br>Arg | acg<br>Thr | 815 |
| tgg<br>Trp | tcc<br>Ser<br>195 | cag<br>Gln | tgt<br>Cys | gtg<br>Val | acc<br>Thr | aac<br>Asn<br>200 | cac<br>His | acg<br>Thr | ctg<br>Leu | gtg<br>Val | ctc<br>Leu<br>205 | acc<br>Thr | tgg<br>Trp | ctg<br>Leu | gag<br>Glu | 863 |
| ccg<br>Pro<br>210 | aac<br>Asn | act<br>Thr | ctt<br>Leu | tac<br>Tyr | tgc<br>Cys<br>215 | gta<br>Val | cac<br>His | gtg<br>Val | gag<br>Glu | tcc<br>Ser<br>220 | ttc<br>Phe | gtc<br>Val | cca<br>Pro | ggg<br>Gly | ccc<br>Pro<br>225 | 911 |
| cct<br>Pro | cgc<br>Arg | cgt<br>Arg | gct<br>Ala | cag<br>Gln<br>230 | cct<br>Pro | tct<br>Ser | gag<br>Glu | aag<br>Lys | cag<br>Gln<br>235 | tgt<br>Cys | gcc<br>Ala | agg<br>Arg | act<br>Thr | ttg<br>Leu<br>240 | aaa<br>Lys | 959 |
| gat<br>Asp | caa<br>Gln | tca<br>Ser | tca<br>Ser<br>245 | gag<br>Glu | ttc<br>Phe | aag<br>Lys | gct<br>Ala | aaa<br>Lys<br>250 | atc<br>Ile | atc<br>Ile | ttc<br>Phe | tgg<br>Trp | tat<br>Tyr<br>255 | gtt<br>Val | ttg<br>Leu | 1007 |
| ccc<br>Pro | ata<br>Ile | tct<br>Ser<br>260 | att<br>Ile | acc<br>Thr | gtg<br>Val | ttt<br>Phe | ctt<br>Leu<br>265 | ttt<br>Phe | tct<br>Ser | gtg<br>Val | atg<br>Met | ggc<br>Gly<br>270 | tat<br>Tyr | tcc<br>Ser | atc<br>Ile | 1055 |

```
tac cga tat atc cac gtt ggc aaa gag aaa cac cca gca aat ttg att    1103
Tyr Arg Tyr Ile His Val Gly Lys Glu Lys His Pro Ala Asn Leu Ile
275                 280                 285 ttg att tat gga aat gaa ttt gac aaa aga ttc ttt gtg cct gct gaa    1151
Leu Ile Tyr Gly Asn Glu Phe Asp Lys Arg Phe Phe Val Pro Ala Glu
290                 295                 300                 305 aaa atc gtg att aac ttt atc acc ctc aat atc tcg gat gat tct aaa    1199
Lys Ile Val Ile Asn Phe Ile Thr Leu Asn Ile Ser Asp Asp Ser Lys
    310                 315                 320 att tct cat cag gat atg agt tta ctg gga aaa agc agt gat gta tcc    1247
Ile Ser His Gln Asp Met Ser Leu Leu Gly Lys Ser Ser Asp Val Ser
        325                 330                 335 agc ctt aat gat cct cag ccc agc ggg aac ctg agg ccc cct cag gag    1295
Ser Leu Asn Asp Pro Gln Pro Ser Gly Asn Leu Arg Pro Pro Gln Glu
            340                 345                 350 gaa gag gag gtg aaa cat tta ggg tat gct tcg cat ttg atg gaa att    1343
Glu Glu Glu Val Lys His Leu Gly Tyr Ala Ser His Leu Met Glu Ile
355                 360                 365 ttt tgt gac tct gaa gaa aac acg gaa ggt act tct ttc acc cag caa    1391
Phe Cys Asp Ser Glu Glu Asn Thr Glu Gly Thr Ser Phe Thr Gln Gln
370                 375                 380                 385 gag tcc ctc agc aga aca ata ccc ccg gat aaa aca gtc att gaa tat    1439
Glu Ser Leu Ser Arg Thr Ile Pro Pro Asp Lys Thr Val Ile Glu Tyr
        390                 395                 400 gaa tat gat gtc aga acc act gac att tgt gcg ggg cct gaa gag cag    1487
Glu Tyr Asp Val Arg Thr Thr Asp Ile Cys Ala Gly Pro Glu Glu Gln
            405                 410                 415 gag ctc agt ttg cag gag gag gtg tcc aca caa gga aca tta ttg gag    1535
Glu Leu Ser Leu Gln Glu Glu Val Ser Thr Gln Gly Thr Leu Leu Glu
                420                 425                 430 tcg cag gca gcg ttg gca gtc ttg ggc ccg caa acg tta cag tac tca    1583
Ser Gln Ala Ala Leu Ala Val Leu Gly Pro Gln Thr Leu Gln Tyr Ser
435                 440                 445 tac acc cct cag ctc caa gac tta gac ccc ctg gcg cag gag cac aca    1631
Tyr Thr Pro Gln Leu Gln Asp Leu Asp Pro Leu Ala Gln Glu His Thr
450                 455                 460                 465 gac tcg gag gag ggg ccg gag gaa gag cca tcg acg acc ctg gtc gac    1679
Asp Ser Glu Glu Gly Pro Glu Glu Glu Pro Ser Thr Thr Leu Val Asp
        470                 475                 480 tgg gat ccc caa act ggc agg ctg tgt att cct tcg ctg tcc agc ttc    1727
Trp Asp Pro Gln Thr Gly Arg Leu Cys Ile Pro Ser Leu Ser Ser Phe
            485                 490                 495 gac cag gat tca gag ggc tgc gag cct tct gag ggg gat ggg ctc gga    1775
Asp Gln Asp Ser Glu Gly Cys Glu Pro Ser Glu Gly Asp Gly Leu Gly
                500                 505                 510 gag gag ggt ctt cta tct aga ctc tat gag gag ccg gct cca gac agg    1823
Glu Glu Gly Leu Leu Ser Arg Leu Tyr Glu Glu Pro Ala Pro Asp Arg
515                 520                 525 cca cca gga gaa aat gaa acc tat ctc atg caa ttc atg gag gaa tgg    1871
Pro Pro Gly Glu Asn Glu Thr Tyr Leu Met Gln Phe Met Glu Glu Trp
530                 535                 540                 545 ggg tta tat gtg cag atg gaa aac tgatgccaac acttccttt gcctttgtt    1925
Gly Leu Tyr Val Gln Met Glu Asn
        550 tcctgtgcaa acaagtgagt caccccttg atcccagcca taaagtacct gggatgaaag   1985 aagttttttc cagtttgtca gtgtctgtga gaattactta tttcttttct ctattctcat   2045 agcacgtgtg tgattggttc atgcatgtag gtctcttaac aatgatggtg ggcctctgga   2105 gtccaggggc tggccggttg ttctatgcag agaaagcagt caataaatgt ttgccagact   2165
```

-continued

```
gggtgcagaa tttattcagg tgggtgtact ctggcctctt ggttcattat tttcaaacaa    2225
gcacacttgt acaattattt tctgggtact tcccatatgc acatagcact gtaaaaaata    2285
tttcccaaag atcactcatt ttataaatac cactttttca gaattgggtt tattgcgagc    2345
aggaggagat acttaaaaca tgcacatata ccaggttggt ggtaagttgg tcacatgtga    2405
aaacctcaac tatttaatca tcatgattca tattttgagt gaatacatca ggcacagacc    2465
ttcatgatat cacacactct tggctacttt aagaggccat ctttaatact ttatgagtag    2525
ttctggagtg taaacataaa cgagtattct tttgtagtca gaaaagtgtc ctctcaataa    2585
tttagtaggg gcttattgtc tctcaaaact aacctaaaag aaaatgacac attttataat    2645
agaatattac atttatttct ggaagtgtgt tttcaaaaag atatttacat agtctgtaaa    2705
ctagaaagtg ttaggtaaag ctctaggtta ctgtgttact attataatat taaacattcg    2765
aataggcagt cgttcaaaga ctctttggaa tatctatgaa tgaatatcct ctattcttat    2825
aatattaaaa cccataagta aatataggac atacaagaga aatgagttaa atgactatgt    2885
aagggagagt ttattaaaat ttgatgaaat ttactgtagg aactaaacta tgccataaaa    2945
caatagcttt ctagttcatt tccagtaact gttcccatct cctttaccac ttgttaagaa    3005
aattaaattc ttcagtcacg ctgctttaaa atgggacaaa atctattaag ttgaaccata    3065
tataattgtg gatatttggc tgttttaat ctgacaagca gtaacttcat atggtttgcc     3125
ttaatatata tttgttttag tcatgaactc ataatccatt gatgctcttt catgagaaga    3185
gatatgaccc atatttcctt attgatatta ttggtacagg cagacaaccc tggtaggaga    3245
gatggattct ggggtcatga cctttcgtga ttatccgcaa atgcaaacag tttcagatct    3305
aatggtttaa tttagggagt aattatatta atcagagtgt tctgttattc tcaatctttta   3365 tagaaacgat tctgctggtt ttgaagaaca gatgtattac actaactgta aaagtagttc    3425
aagagtgaga aagaataaat tgttattaag agcaaaagaa aaataaagtg attgatgata    3485
aaaaaaaaaa aaaaaaagcg gccgcctcga g                                   3516
```

<210> SEQ ID NO 2
<211> LENGTH: 553
<212> TYPE: PRT
<213> ORGANISM: Homo sapiens

<400> SEQUENCE: 2

```
Met Arg Ala Pro Gly Arg Pro Ala Leu Arg Pro Leu Pro Leu Pro Pro
  1               5                  10                  15

Leu Leu Leu Leu Leu Leu Ala Ala Pro Trp Gly Arg Ala Val Pro Cys
             20                  25                  30

Val Ser Gly Gly Leu Pro Lys Pro Ala Asn Ile Thr Phe Leu Ser Ile
         35                  40                  45

Asn Met Lys Asn Val Leu Gln Trp Thr Pro Pro Glu Gly Leu Gln Gly
     50                  55                  60

Val Lys Val Thr Tyr Thr Val Gln Tyr Phe Ile Tyr Gly Gln Lys Lys
 65                  70                  75                  80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
        115                 120                 125
```

-continued

```
Phe Tyr Pro Phe Leu Glu Thr Gln Ile Gly Pro Pro Glu Val Ala Leu
    130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
    210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
        275                 280                 285

Ile Leu Ile Tyr Gly Asn Glu Phe Asp Lys Arg Phe Phe Val Pro Ala
    290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
            340                 345                 350

Glu Glu Glu Glu Val Lys His Leu Gly Tyr Ala Ser His Leu Met Glu
        355                 360                 365

Ile Phe Cys Asp Ser Glu Glu Asn Thr Glu Gly Thr Ser Phe Thr Gln
    370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
            420                 425                 430

Glu Ser Gln Ala Ala Leu Ala Val Leu Gly Pro Gln Thr Leu Gln Tyr
        435                 440                 445

Ser Tyr Thr Pro Gln Leu Gln Asp Leu Asp Pro Leu Ala Gln Glu His
    450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
            500                 505                 510

Gly Glu Glu Gly Leu Leu Ser Arg Leu Tyr Glu Glu Pro Ala Pro Asp
        515                 520                 525

Arg Pro Pro Gly Glu Asn Glu Thr Tyr Leu Met Gln Phe Met Glu Glu
    530                 535                 540

Trp Gly Leu Tyr Val Gln Met Glu Asn
```

<210> SEQ ID NO 3
<211> LENGTH: 221
<212> TYPE: PRT
<213> ORGANISM: Homo sapiens

<400> SEQUENCE: 3

```
Val Pro Cys Val Ser Gly Gly Leu Pro Lys Pro Ala Asn Ile Thr Phe
  1               5                  10                  15

Leu Ser Ile Asn Met Lys Asn Val Leu Gln Trp Thr Pro Pro Glu Gly
             20                  25                  30

Leu Gln Gly Val Lys Val Thr Tyr Thr Val Gln Tyr Phe Ile Tyr Gly
         35                  40                  45

Gln Lys Lys Trp Leu Asn Lys Ser Glu Cys Arg Asn Ile Asn Arg Thr
 50                  55                  60

Tyr Cys Asp Leu Ser Ala Glu Thr Ser Asp Tyr Glu His Gln Tyr Tyr
 65                  70                  75                  80

Ala Lys Val Lys Ala Ile Trp Gly Thr Lys Cys Ser Lys Trp Ala Glu
                 85                  90                  95

Ser Gly Arg Phe Tyr Pro Phe Leu Glu Thr Gln Ile Gly Pro Pro Glu
            100                 105                 110

Val Ala Leu Thr Thr Asp Glu Lys Ser Ile Ser Val Val Leu Thr Ala
        115                 120                 125

Pro Glu Lys Trp Lys Arg Asn Pro Glu Asp Leu Pro Val Ser Met Gln
    130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
        195                 200                 205

Arg Thr Leu Lys Asp Gln Ser Ser Glu Phe Lys Ala Lys
    210                 215                 220
```

<210> SEQ ID NO 4
<211> LENGTH: 971
<212> TYPE: DNA
<213> ORGANISM: Homo sapiens
<220> FEATURE:
<221> NAME/KEY: CDS
<222> LOCATION: (18)...(950)

<400> SEQUENCE: 4

```
gaattcgagt ctaccaa atg cag act ttc aca atg gtt cta gaa gaa atc     50
                   Met Gln Thr Phe Thr Met Val Leu Glu Glu Ile
                     1               5                  10 tgg aca agt ctt ttc atg tgg ttt ttc tac gca ttg att cca tgt ttg     98
Trp Thr Ser Leu Phe Met Trp Phe Phe Tyr Ala Leu Ile Pro Cys Leu
             15                  20                  25 ctc aca gat gaa gtg gcc att ctg cct gcc cct cag aac ctc tct gta    146
Leu Thr Asp Glu Val Ala Ile Leu Pro Ala Pro Gln Asn Leu Ser Val
         30                  35                  40 ctc tca acc aac atg aag cat ctc ttg atg tgg agc cca gtg atc gcg    194
Leu Ser Thr Asn Met Lys His Leu Leu Met Trp Ser Pro Val Ile Ala
     45                  50                  55
```

```
cct gga gaa aca gtg tac tat tct gtc gaa tac cag ggg gag tac gag      242
Pro Gly Glu Thr Val Tyr Tyr Ser Val Glu Tyr Gln Gly Glu Tyr Glu
 60              65                  70                  75 agc ctg tac acg agc cac atc tgg atc ccc agc agc tgg tgc tca ctc      290
Ser Leu Tyr Thr Ser His Ile Trp Ile Pro Ser Ser Trp Cys Ser Leu
             80                  85                  90 act gaa ggt cct gag tgt gat gtc act gat gac atc acg gcc act gtg      338
Thr Glu Gly Pro Glu Cys Asp Val Thr Asp Asp Ile Thr Ala Thr Val
         95                 100                 105 cca tac aac ctt cgt gtc agg gcc aca ttg ggc tca cag acc tca gcc      386
Pro Tyr Asn Leu Arg Val Arg Ala Thr Leu Gly Ser Gln Thr Ser Ala
    110                 115                 120 tgg agc atc ctg aag cat ccc ttt aat aga aac tca acc atc ctt acc      434
Trp Ser Ile Leu Lys His Pro Phe Asn Arg Asn Ser Thr Ile Leu Thr
125                 130                 135 cga cct ggg atg gag atc acc aaa gat ggc ttc cac ctg gtt att gag      482
Arg Pro Gly Met Glu Ile Thr Lys Asp Gly Phe His Leu Val Ile Glu
140                 145                 150                 155 ctg gag gac ctg ggg ccc cag ttt gag ttc ctt gtg gcc tac tgg agg      530
Leu Glu Asp Leu Gly Pro Gln Phe Glu Phe Leu Val Ala Tyr Trp Arg
                160                 165                 170 agg gag cct ggt gcc gag gaa cat gtc aaa atg gtg agg agt ggg ggt      578
Arg Glu Pro Gly Ala Glu Glu His Val Lys Met Val Arg Ser Gly Gly
            175                 180                 185 att cca gtg cac cta gaa acc atg gag cca ggg gct gca tac tgt gtg      626
Ile Pro Val His Leu Glu Thr Met Glu Pro Gly Ala Ala Tyr Cys Val
        190                 195                 200 aag gcc cag aca ttc gtg aag gcc att ggg agg tac agc gcc ttc agc      674
Lys Ala Gln Thr Phe Val Lys Ala Ile Gly Arg Tyr Ser Ala Phe Ser
    205                 210                 215 cag aca gaa tgt gtg gag gtg caa gga gag gcc att ccc ctg gta ctg      722
Gln Thr Glu Cys Val Glu Val Gln Gly Glu Ala Ile Pro Leu Val Leu
220                 225                 230                 235 gcc ctg ttt gcc ttt gtt ggc ttc atg ctg atc ctt gtg gtc gtg cca      770
Ala Leu Phe Ala Phe Val Gly Phe Met Leu Ile Leu Val Val Val Pro
                240                 245                 250 ctg ttc gtc tgg aaa atg ggc cgg ctg ctc cag tac tcc tgt tgc ccc      818
Leu Phe Val Trp Lys Met Gly Arg Leu Leu Gln Tyr Ser Cys Cys Pro
            255                 260                 265 gtg gtg gtc ctc cca gac acc ttg aaa ata acc aat tca ccc cag aag      866
Val Val Val Leu Pro Asp Thr Leu Lys Ile Thr Asn Ser Pro Gln Lys
        270                 275                 280 tta atc agc tgc aga agg gag gag gtg gat gcc tgt gcc acg gct gtg      914
Leu Ile Ser Cys Arg Arg Glu Glu Val Asp Ala Cys Ala Thr Ala Val
285                 290                 295 atg tct cct gag gaa ctc ctc agg gcc tgg atc tca taggtttgcg           960
Met Ser Pro Glu Glu Leu Leu Arg Ala Trp Ile Ser
300                 305                 310 gaaggctcga g                                                         971

<210> SEQ ID NO 5
<211> LENGTH: 311
<212> TYPE: PRT
<213> ORGANISM: Homo sapiens

<400> SEQUENCE: 5

Met Gln Thr Phe Thr Met Val Leu Glu Glu Ile Trp Thr Ser Leu Phe
 1               5                  10                  15

Met Trp Phe Phe Tyr Ala Leu Ile Pro Cys Leu Leu Thr Asp Glu Val
                20                  25                  30
```

```
Ala Ile Leu Pro Ala Pro Gln Asn Leu Ser Val Leu Ser Thr Asn Met
         35                  40                  45

Lys His Leu Leu Met Trp Ser Pro Val Ile Ala Pro Gly Glu Thr Val
 50                  55                  60

Tyr Tyr Ser Val Glu Tyr Gln Gly Glu Tyr Glu Ser Leu Tyr Thr Ser
 65                  70                  75                  80

His Ile Trp Ile Pro Ser Ser Trp Cys Ser Leu Thr Glu Gly Pro Glu
                 85                  90                  95

Cys Asp Val Thr Asp Asp Ile Thr Ala Thr Val Pro Tyr Asn Leu Arg
             100                 105                 110

Val Arg Ala Thr Leu Gly Ser Gln Thr Ser Ala Trp Ser Ile Leu Lys
         115                 120                 125

His Pro Phe Asn Arg Asn Ser Thr Ile Leu Thr Arg Pro Gly Met Glu
     130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Ile Pro Leu Val Leu Ala Leu Phe Ala Phe
225                 230                 235                 240

Val Gly Phe Met Leu Ile Leu Val Val Pro Leu Phe Val Trp Lys
                245                 250                 255

Met Gly Arg Leu Leu Gln Tyr Ser Cys Cys Pro Val Val Val Leu Pro
                260                 265                 270

Asp Thr Leu Lys Ile Thr Asn Ser Pro Gln Lys Leu Ile Ser Cys Arg
            275                 280                 285

Arg Glu Glu Val Asp Ala Cys Ala Thr Ala Val Met Ser Pro Glu Glu
        290                 295                 300

Leu Leu Arg Ala Trp Ile Ser
305                 310

<210> SEQ ID NO 6
<211> LENGTH: 203
<212> TYPE: PRT
<213> ORGANISM: Homo sapiens

<400> SEQUENCE: 6

Asp Glu Val Ala Ile Leu Pro Ala Pro Gln Asn Leu Ser Val Leu Ser
  1               5                  10                  15

Thr Asn Met Lys His Leu Leu Met Trp Ser Pro Val Ile Ala Pro Gly
             20                  25                  30

Glu Thr Val Tyr Tyr Ser Val Glu Tyr Gln Gly Glu Tyr Glu Ser Leu
         35                  40                  45

Tyr Thr Ser His Ile Trp Ile Pro Ser Ser Trp Cys Ser Leu Thr Glu
 50                  55                  60

Gly Pro Glu Cys Asp Val Thr Asp Asp Ile Thr Ala Thr Val Pro Tyr
 65                  70                  75                  80

Asn Leu Arg Val Arg Ala Thr Leu Gly Ser Gln Thr Ser Ala Trp Ser
```

```
                 85                  90                  95
Ile Leu Lys His Pro Phe Asn Arg Asn Ser Thr Ile Leu Thr Arg Pro
            100                 105                 110
Gly Met Glu Ile Thr Lys Asp Gly Phe His Leu Val Ile Glu Leu Glu
            115                 120                 125
Asp Leu Gly Pro Gln Phe Glu Phe Leu Val Ala Tyr Trp Arg Arg Glu
            130                 135                 140
Pro Gly Ala Glu Glu His Val Lys Met Val Arg Ser Gly Gly Ile Pro
145                 150                 155                 160
Val His Leu Glu Thr Met Glu Pro Gly Ala Ala Tyr Cys Val Lys Ala
            165                 170                 175
Gln Thr Phe Val Lys Ala Ile Gly Arg Tyr Ser Ala Phe Ser Gln Thr
            180                 185                 190
Glu Cys Val Glu Val Gln Gly Glu Ala Ile Pro
            195                 200

<210> SEQ ID NO 7
<211> LENGTH: 33
<212> TYPE: DNA
<213> ORGANISM: Homo sapiens

<400> SEQUENCE: 7
gcgaattcga gtctaccaaa tgcagacttt cac                          33

<210> SEQ ID NO 8
<211> LENGTH: 32
<212> TYPE: DNA
<213> ORGANISM: Homo sapiens

<400> SEQUENCE: 8
cgctcgagcc ttccgcaaac ctatgagatc ca                           32

<210> SEQ ID NO 9
<211> LENGTH: 29
<212> TYPE: DNA
<213> ORGANISM: Homo sapiens

<400> SEQUENCE: 9
ggccggccat gcagactttc acaatggtt                               29

<210> SEQ ID NO 10
<211> LENGTH: 52
<212> TYPE: DNA
<213> ORGANISM: Homo sapiens

<400> SEQUENCE: 10
tccgctaccg ccgcctccac tgccaccacc tccggcctct ccttgcacct cc      52

<210> SEQ ID NO 11
<211> LENGTH: 53
<212> TYPE: DNA
<213> ORGANISM: Homo sapiens

<400> SEQUENCE: 11
gtggaggcgg cggtagcgga ggcggtggca gtcgaactgt ggctgcacca tct     53

<210> SEQ ID NO 12
<211> LENGTH: 38
<212> TYPE: DNA
<213> ORGANISM: Homo sapiens
```

```
<400> SEQUENCE: 12
ggcgcgcctc tagattaaca ctctcccctg ttgaagct                          38

<210> SEQ ID NO 13
<211> LENGTH: 30
<212> TYPE: DNA
<213> ORGANISM: Homo sapiens

<400> SEQUENCE: 13
gtcgaccatg gatgcaatga agagagggct                                  30

<210> SEQ ID NO 14
<211> LENGTH: 30
<212> TYPE: DNA
<213> ORGANISM: Homo sapiens

<400> SEQUENCE: 14
cacagggaac tctacggaag cgtctcaact                                  30

<210> SEQ ID NO 15
<211> LENGTH: 33
<212> TYPE: DNA
<213> ORGANISM: Homo sapiens

<400> SEQUENCE: 15
cttccgtaga gttccctgtg tctctggtgg ttt                              33

<210> SEQ ID NO 16
<211> LENGTH: 53
<212> TYPE: DNA
<213> ORGANISM: Homo sapiens

<400> SEQUENCE: 16
gccagagcca cctccgcctg aaccgcctcc accttgatct ttcaaagtcc tgg        53

<210> SEQ ID NO 17
<211> LENGTH: 51
<212> TYPE: DNA
<213> ORGANISM: Homo sapiens

<400> SEQUENCE: 17
caggcggagg tggctctggc ggtggcggat cggcctccac caagggccca t          51

<210> SEQ ID NO 18
<211> LENGTH: 20
<212> TYPE: DNA
<213> ORGANISM: Homo sapiens

<400> SEQUENCE: 18
ctgggcacgg tgggcatgtg                                             20

<210> SEQ ID NO 19
<211> LENGTH: 20
<212> TYPE: DNA
<213> ORGANISM: Homo sapiens

<400> SEQUENCE: 19
cacatgccca ccgtgcccag                                             20

<210> SEQ ID NO 20
<211> LENGTH: 31
<212> TYPE: DNA
<213> ORGANISM: Homo sapiens
```

-continued

<400> SEQUENCE: 20
agatctagat tatttacccg gagacaggga g                                  31

<210> SEQ ID NO 21
<211> LENGTH: 1081
<212> TYPE: DNA
<213> ORGANISM: Homo sapiens
<220> FEATURE:
<221> NAME/KEY: CDS
<222> LOCATION: (9)...(1067)

<400> SEQUENCE: 21

```
ggccggcc atg cag act ttc aca atg gtt cta gaa gaa atc tgg aca agt        50
         Met Gln Thr Phe Thr Met Val Leu Glu Glu Ile Trp Thr Ser
          1               5                  10 ctt ttc atg tgg ttt ttc tac gca ttg att cca tgt ttg ctc aca gat         98
Leu Phe Met Trp Phe Phe Tyr Ala Leu Ile Pro Cys Leu Leu Thr Asp
 15              20                  25                  30 gaa gtg gcc att ctg cct gcc cct cag aac ctc tct gta ctc tca acc        146
Glu Val Ala Ile Leu Pro Ala Pro Gln Asn Leu Ser Val Leu Ser Thr
             35                  40                  45 aac atg aag cat ctc ttg atg tgg agc cca gtg atc gcg cct gga gaa        194
Asn Met Lys His Leu Leu Met Trp Ser Pro Val Ile Ala Pro Gly Glu
         50                  55                  60 aca gtg tac tat tct gtc gaa tac cag ggg gag tac gag agc ctg tac        242
Thr Val Tyr Tyr Ser Val Glu Tyr Gln Gly Glu Tyr Glu Ser Leu Tyr
     65                  70                  75 acg agc cac atc tgg atc ccc agc agc tgg tgc tca ctc act gaa ggt        290
Thr Ser His Ile Trp Ile Pro Ser Ser Trp Cys Ser Leu Thr Glu Gly
 80                  85                  90 cct gag tgt gat gtc act gat gac atc acg gcc act gtg cca tac aac        338
Pro Glu Cys Asp Val Thr Asp Asp Ile Thr Ala Thr Val Pro Tyr Asn
 95                 100                 105                 110 ctt cgt gtc agg gcc aca ttg ggc tca cag acc tca gcc tgg agc atc        386
Leu Arg Val Arg Ala Thr Leu Gly Ser Gln Thr Ser Ala Trp Ser Ile
                115                 120                 125 ctg aag cat ccc ttt aat aga aac tca acc atc ctt acc cga cct ggg        434
Leu Lys His Pro Phe Asn Arg Asn Ser Thr Ile Leu Thr Arg Pro Gly
            130                 135                 140 atg gag atc ccc aaa cat ggc ttc cac ctg gtt att gag ctg gag gac        482
Met Glu Ile Pro Lys His Gly Phe His Leu Val Ile Glu Leu Glu Asp
        145                 150                 155 ctg ggg ccc cag ttt gag ttc ctt gtg gcc tac tgg acg agg gag cct        530
Leu Gly Pro Gln Phe Glu Phe Leu Val Ala Tyr Trp Thr Arg Glu Pro
    160                 165                 170 ggt gcc gag gaa cat gtc aaa atg gtg agg agt ggg ggt att cca gtg        578
Gly Ala Glu Glu His Val Lys Met Val Arg Ser Gly Gly Ile Pro Val
175                 180                 185                 190 cac cta gaa acc atg gag cca ggg gct gca tac tgt gtg aag gcc cag        626
His Leu Glu Thr Met Glu Pro Gly Ala Ala Tyr Cys Val Lys Ala Gln
                195                 200                 205 aca ttc gtg aag gcc att ggg agg tac agc gcc ttc agc cag aca gaa        674
Thr Phe Val Lys Ala Ile Gly Arg Tyr Ser Ala Phe Ser Gln Thr Glu
            210                 215                 220 tgt gtg gag gtg caa gga gag gcc gga ggt ggc agt gga ggc ggc            722
Cys Val Glu Val Gln Gly Glu Ala Gly Gly Gly Ser Gly Gly Gly
        225                 230                 235 ggt agc gga ggc ggt ggc agt cga act gtg gct gca cca tct gtc ttc        770
Gly Ser Gly Gly Gly Gly Ser Arg Thr Val Ala Ala Pro Ser Val Phe
    240                 245                 250
```

```
atc ttc ccg cca tct gat gag cag ttg aaa tct gga act gcc tct gtt      818
Ile Phe Pro Pro Ser Asp Glu Gln Leu Lys Ser Gly Thr Ala Ser Val
255                 260                 265                 270 gtg tgc ctg ctg aat aac ttc tat ccc aga gag gcc aaa gta cag tgg      866
Val Cys Leu Leu Asn Asn Phe Tyr Pro Arg Glu Ala Lys Val Gln Trp
            275                 280                 285 aag gtg gat aac gcc ctc caa tcg ggt aac tcc cag gag agt gtc aca      914
Lys Val Asp Asn Ala Leu Gln Ser Gly Asn Ser Gln Glu Ser Val Thr
290                 295                 300 gag cag gac agc aag gac agc acc tac agc ctc agc agc acc ctg acg      962
Glu Gln Asp Ser Lys Asp Ser Thr Tyr Ser Leu Ser Ser Thr Leu Thr
        305                 310                 315 ctg agc aaa gca gac tac gag aaa cac aaa gtc tac gcc tgc gaa gtc     1010
Leu Ser Lys Ala Asp Tyr Glu Lys His Lys Val Tyr Ala Cys Glu Val
320                 325                 330 acc cat cag ggc ctg agc tcg ccc gtc aca aag agc ttc aac agg gga     1058
Thr His Gln Gly Leu Ser Ser Pro Val Thr Lys Ser Phe Asn Arg Gly
335                 340                 345                 350 gag tgt taa tctagaggcg cgcc                                         1081
Glu Cys  *

<210> SEQ ID NO 22
<211> LENGTH: 352
<212> TYPE: PRT
<213> ORGANISM: Homo sapiens

<400> SEQUENCE: 22

Met Gln Thr Phe Thr Met Val Leu Glu Glu Ile Trp Thr Ser Leu Phe
1               5                   10                  15

Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Glu Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Pro Lys His Gly Phe His Leu Val Ile Glu Leu Glu Asp Leu Gly
145                 150                 155                 160

Pro Gln Phe Glu Phe Leu Val Ala Tyr Trp Thr Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Gly Gly Gly Ser Gly Gly Gly Gly Ser
```

```
                225                 230                 235                 240
Gly Gly Gly Gly Ser Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
        275                 280                 285

Asp Asn Ala Leu Gln Ser Gly Asn Ser Gln Glu Ser Val Thr Glu Gln
    290                 295                 300

Asp Ser Lys Asp Ser Thr Tyr Ser Leu Ser Ser Thr Leu Thr Leu Ser
305                 310                 315                 320

Lys Ala Asp Tyr Glu Lys His Lys Val Tyr Ala Cys Glu Val Thr His
                325                 330                 335

Gln Gly Leu Ser Ser Pro Val Thr Lys Ser Phe Asn Arg Gly Glu Cys
                340                 345                 350

<210> SEQ ID NO 23
<211> LENGTH: 1801
<212> TYPE: DNA
<213> ORGANISM: Homo sapiens
<220> FEATURE:
<221> NAME/KEY: CDS
<222> LOCATION: (8)...(1789)

<400> SEQUENCE: 23 gtcgacc atg gat gca atg aag aga ggg ctc tgc tgt gtg ctg ctg ctg       49
        Met Asp Ala Met Lys Arg Gly Leu Cys Cys Val Leu Leu Leu
        1               5                   10 tgt ggc gcc gtc ttc gtt tcg ctc agc cag gaa atc cat gcc gag ttg       97
Cys Gly Ala Val Phe Val Ser Leu Ser Gln Glu Ile His Ala Glu Leu
15                  20                  25                  30 aga cgc ttc cgt aga gtt ccc tgt gtc tct ggt ggt ttg cct aaa cct      145
Arg Arg Phe Arg Arg Val Pro Cys Val Ser Gly Gly Leu Pro Lys Pro
                35                  40                  45 gca aac atc acc ttc tta tcc atc aac atg aag aat gtc cta caa tgg      193
Ala Asn Ile Thr Phe Leu Ser Ile Asn Met Lys Asn Val Leu Gln Trp
            50                  55                  60 act cca cca gag ggt ctt caa gga gtt aaa gtt act tac act gtg cag      241
Thr Pro Pro Glu Gly Leu Gln Gly Val Lys Val Thr Tyr Thr Val Gln
        65                  70                  75 tat ttc ata tat ggg caa aag aaa tgg ctg aat aaa tca gaa tgc aga      289
Tyr Phe Ile Tyr Gly Gln Lys Lys Trp Leu Asn Lys Ser Glu Cys Arg
    80                  85                  90 aat atc aat aga acc tac tgt gat ctt tct gct gaa act tct gac tac      337
Asn Ile Asn Arg Thr Tyr Cys Asp Leu Ser Ala Glu Thr Ser Asp Tyr
95                  100                 105                 110 gaa cac cag tat tat gcc aaa gtt aag gcc att tgg gga aca aag tgt      385
Glu His Gln Tyr Tyr Ala Lys Val Lys Ala Ile Trp Gly Thr Lys Cys
                115                 120                 125 tcc aaa tgg gct gaa agt gga cgg ttc tat cct ttt tta gaa aca caa      433
Ser Lys Trp Ala Glu Ser Gly Arg Phe Tyr Pro Phe Leu Glu Thr Gln
            130                 135                 140 att ggc cca cca gag gtg gca ctg act aca gat gag aag tcc att tct      481
Ile Gly Pro Pro Glu Val Ala Leu Thr Thr Asp Glu Lys Ser Ile Ser
        145                 150                 155 gtt gtc ctg aca gct cca gag aag tgg aag aga aat cca gaa gac ctt      529
Val Val Leu Thr Ala Pro Glu Lys Trp Lys Arg Asn Pro Glu Asp Leu
    160                 165                 170 cct gtt tcc atg caa caa ata tac tcc aat ctg aag tat aac gtg tct      577
```

```
                Pro Val Ser Met Gln Gln Ile Tyr Ser Asn Leu Lys Tyr Asn Val Ser
                175                 180                 185                 190 gtg ttg aat act aaa tca aac aga acg tgg tcc cag tgt gtg acc aac          625
Val Leu Asn Thr Lys Ser Asn Arg Thr Trp Ser Gln Cys Val Thr Asn
                    195                 200                 205 cac acg ctg gtg ctc acc tgg ctg gag ccg aac act ctt tac tgc gta          673
His Thr Leu Val Leu Thr Trp Leu Glu Pro Asn Thr Leu Tyr Cys Val
                210                 215                 220 cac gtg gag tcc ttc gtc cca ggg ccc cct cgc cgt gct cag cct tct          721
His Val Glu Ser Phe Val Pro Gly Pro Pro Arg Arg Ala Gln Pro Ser
            225                 230                 235 gag aag cag tgt gcc agg act ttg aaa gat caa ggt gga ggc ggt tca          769
Glu Lys Gln Cys Ala Arg Thr Leu Lys Asp Gln Gly Gly Gly Gly Ser
        240                 245                 250 ggc gga ggt ggc tct ggc ggt ggc gga tcg gcc tcc acc aag ggc cca          817
Gly Gly Gly Gly Ser Gly Gly Gly Gly Ser Ala Ser Thr Lys Gly Pro
255                 260                 265                 270 tcg gtc ttc ccc ctg gca ccc tcc tcc aag agc acc tct ggg ggc aca          865
Ser Val Phe Pro Leu Ala Pro Ser Ser Lys Ser Thr Ser Gly Gly Thr
                275                 280                 285 gcg gcc ctg ggc tgc ctg gtc aag gac tac ttc ccc gaa ccg gtg acg          913
Ala Ala Leu Gly Cys Leu Val Lys Asp Tyr Phe Pro Glu Pro Val Thr
                290                 295                 300 gtg tcg tgg aac tca ggc gcc ctg acc agc ggc gtg cac acc ttc ccg          961
Val Ser Trp Asn Ser Gly Ala Leu Thr Ser Gly Val His Thr Phe Pro
            305                 310                 315 gct gtc cta cag tcc tca gga ctc tac tcc ctc agc agc gtg gtg acc         1009
Ala Val Leu Gln Ser Ser Gly Leu Tyr Ser Leu Ser Ser Val Val Thr
        320                 325                 330 gtg ccc tcc agc agc ttg ggc acc cag acc tac atc tgc aac gtg aat         1057
Val Pro Ser Ser Ser Leu Gly Thr Gln Thr Tyr Ile Cys Asn Val Asn
335                 340                 345                 350 cac aag ccc agc aac acc aag gtg gac aag aaa gtt gag ccc aaa tct         1105
His Lys Pro Ser Asn Thr Lys Val Asp Lys Lys Val Glu Pro Lys Ser
                355                 360                 365 tgt gac aaa act cac aca tgc cca ccg tgc cca gca cct gaa gcc gag         1153
Cys Asp Lys Thr His Thr Cys Pro Pro Cys Pro Ala Pro Glu Ala Glu
                370                 375                 380 ggg gca ccg tca gtc ttc ctc ttc ccc cca aaa ccc aag gac acc ctc         1201
Gly Ala Pro Ser Val Phe Leu Phe Pro Pro Lys Pro Lys Asp Thr Leu
            385                 390                 395 atg atc tcc cgg acc cct gag gtc aca tgc gtg gtg gtg gac gtg agc         1249
Met Ile Ser Arg Thr Pro Glu Val Thr Cys Val Val Val Asp Val Ser
        400                 405                 410 cac gaa gac cct gag gtc aag ttc aac tgg tac gtg gac ggc gtg gag         1297
His Glu Asp Pro Glu Val Lys Phe Asn Trp Tyr Val Asp Gly Val Glu
415                 420                 425                 430 gtg cat aat gcc aag aca aag ccg cgg gag gag cag tac aac agc acg         1345
Val His Asn Ala Lys Thr Lys Pro Arg Glu Glu Gln Tyr Asn Ser Thr
                435                 440                 445 tac cgt gtg gtc agc gtc ctc acc gtc ctg cac cag gac tgg ctg aat         1393
Tyr Arg Val Val Ser Val Leu Thr Val Leu His Gln Asp Trp Leu Asn
                450                 455                 460 ggc aag gag tac aag tgc aag gtc tcc aac aaa gcc ctc cca tcc tcc         1441
Gly Lys Glu Tyr Lys Cys Lys Val Ser Asn Lys Ala Leu Pro Ser Ser
            465                 470                 475 atc gag aaa acc atc tcc aaa gcc aaa ggg cag ccc cga gaa cca cag         1489
Ile Glu Lys Thr Ile Ser Lys Ala Lys Gly Gln Pro Arg Glu Pro Gln
        480                 485                 490
```

```
gtg tac acc ctg ccc cca tcc cgg gat gag ctg acc aag aac cag gtc       1537
Val Tyr Thr Leu Pro Pro Ser Arg Asp Glu Leu Thr Lys Asn Gln Val
495                 500                 505                 510 agc ctg acc tgc ctg gtc aaa ggc ttc tat ccc agc gac atc gcc gtg       1585
Ser Leu Thr Cys Leu Val Lys Gly Phe Tyr Pro Ser Asp Ile Ala Val
                515                 520                 525 gag tgg gag agc aat ggg cag ccg gag aac aac tac aag acc acg cct       1633
Glu Trp Glu Ser Asn Gly Gln Pro Glu Asn Asn Tyr Lys Thr Thr Pro
            530                 535                 540 ccc gtg ctg gac tcc gac ggc tcc ttc ttc ctc tac agc aag ctc acc       1681
Pro Val Leu Asp Ser Asp Gly Ser Phe Phe Leu Tyr Ser Lys Leu Thr
        545                 550                 555 gtg gac aag agc agg tgg cag cag ggg aac gtc ttc tca tgc tcc gtg       1729
Val Asp Lys Ser Arg Trp Gln Gln Gly Asn Val Phe Ser Cys Ser Val
    560                 565                 570 atg cat gag gct ctg cac aac cac tac acg cag aag agc ctc tcc ctg       1777
Met His Glu Ala Leu His Asn His Tyr Thr Gln Lys Ser Leu Ser Leu
575                 580                 585                 590 tct ccg ggt aaa taatctagat ct                                         1801
Ser Pro Gly Lys <210> SEQ ID NO 24
<211> LENGTH: 594
<212> TYPE: PRT
<213> ORGANISM: Homo sapiens

<400> SEQUENCE: 24

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Val Pro Cys Val Ser Gly Gly Leu Pro Lys Pro Ala Asn
        35                  40                  45

Ile Thr Phe Leu Ser Ile Asn Met Lys Asn Val Leu Gln Trp Thr Pro
    50                  55                  60

Pro Glu Gly Leu Gln Gly Val Lys Val Thr Tyr Thr Val Gln Tyr Phe
65                  70                  75                  80

Ile Tyr Gly Gln Lys Lys Trp Leu Asn Lys Ser Glu Cys Arg Asn Ile
                85                  90                  95

Asn Arg Thr Tyr Cys Asp Leu Ser Ala Glu Thr Ser Asp Tyr Glu His
            100                 105                 110

Gln Tyr Tyr Ala Lys Val Lys Ala Ile Trp Gly Thr Lys Cys Ser Lys
        115                 120                 125

Trp Ala Glu Ser Gly Arg Phe Tyr Pro Phe Leu Glu Thr Gln Ile Gly
    130                 135                 140

Pro Pro Glu Val Ala Leu Thr Thr Asp Glu Lys Ser Ile Ser Val Val
145                 150                 155                 160

Leu Thr Ala Pro Glu Lys Trp Lys Arg Asn Pro Glu Asp Leu Pro Val
                165                 170                 175

Ser Met Gln Gln Ile Tyr Ser Asn Leu Lys Tyr Asn Val Ser Val Leu
            180                 185                 190

Asn Thr Lys Ser Asn Arg Thr Trp Ser Gln Cys Val Thr Asn His Thr
        195                 200                 205

Leu Val Leu Thr Trp Leu Glu Pro Asn Thr Leu Tyr Cys Val His Val
    210                 215                 220

Glu Ser Phe Val Pro Gly Pro Pro Arg Arg Ala Gln Pro Ser Glu Lys
225                 230                 235                 240
```

```
Gln Cys Ala Arg Thr Leu Lys Asp Gln Gly Gly Gly Ser Gly Gly
                245                 250                 255

Gly Gly Ser Gly Gly Gly Ser Ala Ser Thr Lys Gly Pro Ser Val
            260                 265                 270

Phe Pro Leu Ala Pro Ser Ser Lys Ser Thr Ser Gly Gly Thr Ala Ala
        275                 280                 285

Leu Gly Cys Leu Val Lys Asp Tyr Phe Pro Glu Pro Val Thr Val Ser
290                 295                 300

Trp Asn Ser Gly Ala Leu Thr Ser Gly Val His Thr Phe Pro Ala Val
305                 310                 315                 320

Leu Gln Ser Ser Gly Leu Tyr Ser Leu Ser Ser Val Val Thr Val Pro
                325                 330                 335

Ser Ser Ser Leu Gly Thr Gln Thr Tyr Ile Cys Asn Val Asn His Lys
            340                 345                 350

Pro Ser Asn Thr Lys Val Asp Lys Lys Val Glu Pro Lys Ser Cys Asp
        355                 360                 365

Lys Thr His Thr Cys Pro Pro Cys Pro Ala Pro Glu Ala Glu Gly Ala
370                 375                 380

Pro Ser Val Phe Leu Phe Pro Pro Lys Pro Lys Asp Thr Leu Met Ile
385                 390                 395                 400

Ser Arg Thr Pro Glu Val Thr Cys Val Val Val Asp Val Ser His Glu
                405                 410                 415

Asp Pro Glu Val Lys Phe Asn Trp Tyr Val Asp Gly Val Glu Val His
            420                 425                 430

Asn Ala Lys Thr Lys Pro Arg Glu Glu Gln Tyr Asn Ser Thr Tyr Arg
        435                 440                 445

Val Val Ser Val Leu Thr Val Leu His Gln Asp Trp Leu Asn Gly Lys
    450                 455                 460

Glu Tyr Lys Cys Lys Val Ser Asn Lys Ala Leu Pro Ser Ser Ile Glu
465                 470                 475                 480

Lys Thr Ile Ser Lys Ala Lys Gly Gln Pro Arg Glu Pro Gln Val Tyr
                485                 490                 495

Thr Leu Pro Pro Ser Arg Asp Glu Leu Thr Lys Asn Gln Val Ser Leu
            500                 505                 510

Thr Cys Leu Val Lys Gly Phe Tyr Pro Ser Asp Ile Ala Val Glu Trp
        515                 520                 525

Glu Ser Asn Gly Gln Pro Glu Asn Asn Tyr Lys Thr Thr Pro Pro Val
    530                 535                 540

Leu Asp Ser Asp Gly Ser Phe Phe Leu Tyr Ser Lys Leu Thr Val Asp
545                 550                 555                 560

Lys Ser Arg Trp Gln Gln Gly Asn Val Phe Ser Cys Ser Val Met His
                565                 570                 575

Glu Ala Leu His Asn His Tyr Thr Gln Lys Ser Leu Ser Leu Ser Pro
            580                 585                 590

Gly Lys

<210> SEQ ID NO 25
<211> LENGTH: 36
<212> TYPE: DNA
<213> ORGANISM: Homo sapiens

<400> SEQUENCE: 25
acttgtggaa ttcgctagca ccaagggccc atcggt                    36
```

<210> SEQ ID NO 26
<211> LENGTH: 32
<212> TYPE: DNA
<213> ORGANISM: Homo sapiens

<400> SEQUENCE: 26
gcctagaacg cgttcattta cccggagaca gg                                    32

<210> SEQ ID NO 27
<211> LENGTH: 8
<212> TYPE: DNA
<213> ORGANISM: Homo sapiens

<400> SEQUENCE: 27 aattgaga                                                                8

<210> SEQ ID NO 28
<211> LENGTH: 8
<212> TYPE: DNA
<213> ORGANISM: Homo sapiens

<400> SEQUENCE: 28 cgcgtctc                                                                8

<210> SEQ ID NO 29
<211> LENGTH: 1720
<212> TYPE: DNA
<213> ORGANISM: homo sapiens
<220> FEATURE:
<221> NAME/KEY: CDS
<222> LOCATION: (1)...(1713)

<400> SEQUENCE: 29

```
atg cgg gct ccc ggc cgc ccg gcc ctg cgg ccg ctg ctg ttg ctc           48
Met Arg Ala Pro Gly Arg Pro Ala Leu Arg Pro Leu Leu Leu Leu
 1               5                  10                  15 ctg gcg gcg cct tgg gga cgg gca gtt ccc tgt gtc tct ggt ggt ttg       96
Leu Ala Ala Pro Trp Gly Arg Ala Val Pro Cys Val Ser Gly Gly Leu
             20                  25                  30 cct aaa cct gca aac atc acc ttc tta tcc atc aac atg aag aat gtc      144
Pro Lys Pro Ala Asn Ile Thr Phe Leu Ser Ile Asn Met Lys Asn Val
         35                  40                  45 cta caa tgg act cca cca gag ggt ctt caa gga gtt aaa gtt act tac      192
Leu Gln Trp Thr Pro Pro Glu Gly Leu Gln Gly Val Lys Val Thr Tyr
     50                  55                  60 act gtg cag tat ttc ata tat ggg caa aag aaa tgg ctg aat aaa tca      240
Thr Val Gln Tyr Phe Ile Tyr Gly Gln Lys Lys Trp Leu Asn Lys Ser
 65                  70                  75                  80 gaa tgc aga aat atc aat aga acc tac tgt gat ctt tct gct gaa act      288
Glu Cys Arg Asn Ile Asn Arg Thr Tyr Cys Asp Leu Ser Ala Glu Thr
                 85                  90                  95 tct gac tac gaa cac cag tat tat gcc aaa gtt aag gcc att tgg gga      336
Ser Asp Tyr Glu His Gln Tyr Tyr Ala Lys Val Lys Ala Ile Trp Gly
            100                 105                 110 aca aag tgt tcc aaa tgg gct gaa agt gga cgg ttc tat cct ttt tta      384
Thr Lys Cys Ser Lys Trp Ala Glu Ser Gly Arg Phe Tyr Pro Phe Leu
        115                 120                 125 gaa aca caa att ggc cca cca gag gtg gca ctg act aca gat gag aag      432
Glu Thr Gln Ile Gly Pro Pro Glu Val Ala Leu Thr Thr Asp Glu Lys
    130                 135                 140 tcc att tct gtt gtc ctg aca gct cca gag aag tgg aag aga aat cca      480
Ser Ile Ser Val Val Leu Thr Ala Pro Glu Lys Trp Lys Arg Asn Pro
```

-continued

```
                  145                 150                 155                 160
gaa gac ctt cct gtt tcc atg caa caa ata tac tcc aat ctg aag tat       528
Glu Asp Leu Pro Val Ser Met Gln Gln Ile Tyr Ser Asn Leu Lys Tyr
                165                 170                 175 aac gtg tct gtg ttg aat act aaa tca aac aga acg tgg tcc cag tgt       576
Asn Val Ser Val Leu Asn Thr Lys Ser Asn Arg Thr Trp Ser Gln Cys
            180                 185                 190 gtg acc aac cac acg ctg gtg ctc acc tgg ctg gag ccg aac act ctt       624
Val Thr Asn His Thr Leu Val Leu Thr Trp Leu Glu Pro Asn Thr Leu
        195                 200                 205 tac tgc gta cac gtg gag tcc ttc gtc cca ggg ccc cct cgc cgt gct       672
Tyr Cys Val His Val Glu Ser Phe Val Pro Gly Pro Pro Arg Arg Ala
    210                 215                 220 cag cct tct gag aag cag tgt gcc agg act ttg aaa gat caa tca tca       720
Gln Pro Ser Glu Lys Gln Cys Ala Arg Thr Leu Lys Asp Gln Ser Ser
225                 230                 235                 240 gag gct agc acc aag ggc cca tcg gtc ttc ccc ctg gca ccc tcc tcc       768
Glu Ala Ser Thr Lys Gly Pro Ser Val Phe Pro Leu Ala Pro Ser Ser
                245                 250                 255 aag agc acc tct ggg ggc aca gcg gcc ctg ggc tgc ctg gtc aag gac       816
Lys Ser Thr Ser Gly Gly Thr Ala Ala Leu Gly Cys Leu Val Lys Asp
            260                 265                 270 tac ttc ccc gaa ccg gtg acg gtg tcg tgg aac tca ggc gcc ctg acc       864
Tyr Phe Pro Glu Pro Val Thr Val Ser Trp Asn Ser Gly Ala Leu Thr
        275                 280                 285 agc ggc gtg cac acc ttc ccg gct gtc cta cag tcc tca gga ctc tac       912
Ser Gly Val His Thr Phe Pro Ala Val Leu Gln Ser Ser Gly Leu Tyr
    290                 295                 300 tcc ctc agc agc gtg gtg acc gtg ccc tcc agc agc ttg ggc acc cag       960
Ser Leu Ser Ser Val Val Thr Val Pro Ser Ser Ser Leu Gly Thr Gln
305                 310                 315                 320 acc tac atc tgc aac gtg aat cac aag ccc agc aac acc aag gtg gac      1008
Thr Tyr Ile Cys Asn Val Asn His Lys Pro Ser Asn Thr Lys Val Asp
                325                 330                 335 aag aaa gtt gag ccc aaa tct tgt gac aaa act cac aca tgc cca ccg      1056
Lys Lys Val Glu Pro Lys Ser Cys Asp Lys Thr His Thr Cys Pro Pro
            340                 345                 350 tgc cca gca cct gaa ctc ctg ggg gga ccg tca gtc ttc ctc ttc ccc      1104
Cys Pro Ala Pro Glu Leu Leu Gly Gly Pro Ser Val Phe Leu Phe Pro
        355                 360                 365 cca aaa ccc aag gac acc ctc atg atc tcc cgg acc cct gag gtc aca      1152
Pro Lys Pro Lys Asp Thr Leu Met Ile Ser Arg Thr Pro Glu Val Thr
    370                 375                 380 tgc gtg gtg gtg gac gtg agc cac gaa gac cct gag gtc aag ttc aac      1200
Cys Val Val Val Asp Val Ser His Glu Asp Pro Glu Val Lys Phe Asn
385                 390                 395                 400 tgg tac gtg gac ggc gtg gag gtg cat aat gcc aag aca aag ccg cgg      1248
Trp Tyr Val Asp Gly Val Glu Val His Asn Ala Lys Thr Lys Pro Arg
                405                 410                 415 gag gag cag tac aac agc acg tac cgt gtg gtc agc gtc ctc acc gtc      1296
Glu Glu Gln Tyr Asn Ser Thr Tyr Arg Val Val Ser Val Leu Thr Val
            420                 425                 430 ctg cac cag gac tgg ctg aat ggc aag gag tac aag tgc aag gtc tcc      1344
Leu His Gln Asp Trp Leu Asn Gly Lys Glu Tyr Lys Cys Lys Val Ser
        435                 440                 445 aac aaa gcc ctc cca gcc ccc atc gag aaa acc atc tcc aaa gcc aaa      1392
Asn Lys Ala Leu Pro Ala Pro Ile Glu Lys Thr Ile Ser Lys Ala Lys
    450                 455                 460 ggg cag ccc cga gaa cca cag gtg tac acc ctg ccc cca tcc cgg gat      1440
```

```
Gly Gln Pro Arg Glu Pro Gln Val Tyr Thr Leu Pro Pro Ser Arg Asp
465                 470                 475                 480 gag ctg acc aag aac cag gtc agc ctg acc tgc ctg gtc aaa ggc ttc         1488
Glu Leu Thr Lys Asn Gln Val Ser Leu Thr Cys Leu Val Lys Gly Phe
                485                 490                 495 tat ccc agc gac atc gcc gtg gag tgg gag agc aat ggg cag ccg gag         1536
Tyr Pro Ser Asp Ile Ala Val Glu Trp Glu Ser Asn Gly Gln Pro Glu
            500                 505                 510 aac aac tac aag acc acg cct ccc gtg ctg gac tcc gac ggc tcc ttc         1584
Asn Asn Tyr Lys Thr Thr Pro Pro Val Leu Asp Ser Asp Gly Ser Phe
        515                 520                 525 ttc ctc tac agc aag ctc acc gtg gac aag agc agg tgg cag cag ggg         1632
Phe Leu Tyr Ser Lys Leu Thr Val Asp Lys Ser Arg Trp Gln Gln Gly
    530                 535                 540 aac gtc ttc tca tgc tcc gtg atg cat gag gct ctg cac aac cac tac         1680
Asn Val Phe Ser Cys Ser Val Met His Glu Ala Leu His Asn His Tyr
545                 550                 555                 560 acg cag aag agc ctc tcc ctg tct ccg ggt aaa tgacgcg                     1720
Thr Gln Lys Ser Leu Ser Leu Ser Pro Gly Lys
                565                 570

<210> SEQ ID NO 30
<211> LENGTH: 571
<212> TYPE: PRT
<213> ORGANISM: homo sapiens

<400> SEQUENCE: 30

Met Arg Ala Pro Gly Arg Pro Ala Leu Arg Pro Leu Leu Leu Leu Leu
1               5                   10                  15

Leu Ala Ala Pro Trp Gly Arg Ala Val Pro Cys Val Ser Gly Gly Leu
            20                  25                  30

Pro Lys Pro Ala Asn Ile Thr Phe Leu Ser Ile Asn Met Lys Asn Val
        35                  40                  45

Leu Gln Trp Thr Pro Pro Glu Gly Leu Gln Gly Val Lys Val Thr Tyr
    50                  55                  60

Thr Val Gln Tyr Phe Ile Tyr Gly Gln Lys Lys Trp Leu Asn Lys Ser
65                  70                  75                  80

Glu Cys Arg Asn Ile Asn Arg Thr Tyr Cys Asp Leu Ser Ala Glu Thr
                85                  90                  95

Ser Asp Tyr Glu His Gln Tyr Tyr Ala Lys Val Lys Ala Ile Trp Gly
            100                 105                 110

Thr Lys Cys Ser Lys Trp Ala Glu Ser Gly Arg Phe Tyr Pro Phe Leu
        115                 120                 125

Glu Thr Gln Ile Gly Pro Pro Glu Val Ala Leu Thr Thr Asp Glu Lys
    130                 135                 140

Ser Ile Ser Val Val Leu Thr Ala Pro Glu Lys Trp Lys Arg Asn Pro
145                 150                 155                 160

Glu Asp Leu Pro Val Ser Met Gln Gln Ile Tyr Ser Asn Leu Lys Tyr
                165                 170                 175

Asn Val Ser Val Leu Asn Thr Lys Ser Asn Arg Thr Trp Ser Gln Cys
            180                 185                 190

Val Thr Asn His Thr Leu Val Leu Thr Trp Leu Glu Pro Asn Thr Leu
        195                 200                 205

Tyr Cys Val His Val Glu Ser Phe Val Pro Gly Pro Pro Arg Arg Ala
    210                 215                 220

Gln Pro Ser Glu Lys Gln Cys Ala Arg Thr Leu Lys Asp Gln Ser Ser
225                 230                 235                 240
```

```
Glu Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val Glu Pro Lys Ser Cys Asp Lys Thr His Thr Cys Pro Pro
            340                 345                 350

Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 31
<211> LENGTH: 37
<212> TYPE: DNA
<213> ORGANISM: Homo sapiens

<400> SEQUENCE: 31
gtcacttgaa ttcggtaccg cctctgttgt gtgcctg                                  37

<210> SEQ ID NO 32
<211> LENGTH: 32
<212> TYPE: DNA
<213> ORGANISM: Homo sapiens
```

<400> SEQUENCE: 32
gacctgaacg cgtctaacac tctcccctgt tg         32

<210> SEQ ID NO 33
<211> LENGTH: 1011
<212> TYPE: DNA
<213> ORGANISM: Homo sapiens
<220> FEATURE:
<221> NAME/KEY: CDS
<222> LOCATION: (1)...(1011)

<400> SEQUENCE: 33

| | | | | | | | | | | | | | | | | |
|---|---|---|---|---|---|---|---|---|---|---|---|---|---|---|---|---|
| atg | cag | act | ttc | aca | atg | gtt | cta | gaa | gaa | atc | tgg | aca | agt | ctt | ttc | 48 |
| Met | Gln | Thr | Phe | Thr | Met | Val | Leu | Glu | Glu | Ile | Trp | Thr | Ser | Leu | Phe | |
| 1 | | | | 5 | | | | | 10 | | | | | 15 | | |
| atg | tgg | ttt | ttc | tac | gca | ttg | att | cca | tgt | ttg | ctc | aca | gat | gaa | gtg | 96 |
| Met | Trp | Phe | Phe | Tyr | Ala | Leu | Ile | Pro | Cys | Leu | Leu | Thr | Asp | Glu | Val | |
| | | | 20 | | | | | 25 | | | | | 30 | | | |
| gcc | att | ctg | cct | gcc | cct | cag | aac | ctc | tct | gta | ctc | tca | acc | aac | atg | 144 |
| Ala | Ile | Leu | Pro | Ala | Pro | Gln | Asn | Leu | Ser | Val | Leu | Ser | Thr | Asn | Met | |
| | | 35 | | | | | 40 | | | | | 45 | | | | |
| aag | cat | ctc | ttg | atg | tgg | agc | cca | gtg | atc | gcg | cct | gga | gaa | aca | gtg | 192 |
| Lys | His | Leu | Leu | Met | Trp | Ser | Pro | Val | Ile | Ala | Pro | Gly | Glu | Thr | Val | |
| | 50 | | | | | 55 | | | | | 60 | | | | | |
| tac | tat | tct | gtc | gaa | tac | cag | ggg | gag | tac | gag | agc | ctg | tac | acg | agc | 240 |
| Tyr | Tyr | Ser | Val | Glu | Tyr | Gln | Gly | Glu | Tyr | Glu | Ser | Leu | Tyr | Thr | Ser | |
| 65 | | | | | 70 | | | | | 75 | | | | | 80 | |
| cac | atc | tgg | atc | ccc | agc | agc | tgg | tgc | tca | ctc | act | gaa | ggt | cct | gag | 288 |
| His | Ile | Trp | Ile | Pro | Ser | Ser | Trp | Cys | Ser | Leu | Thr | Glu | Gly | Pro | Glu | |
| | | | | 85 | | | | | 90 | | | | | 95 | | |
| tgt | gat | gtc | act | gat | gac | atc | acg | gcc | act | gtg | cca | tac | aac | ctt | cgt | 336 |
| Cys | Asp | Val | Thr | Asp | Asp | Ile | Thr | Ala | Thr | Val | Pro | Tyr | Asn | Leu | Arg | |
| | | | 100 | | | | | 105 | | | | | 110 | | | |
| gtc | agg | gcc | aca | ttg | ggc | tca | cag | acc | tca | gcc | tgg | agc | atc | ctg | aag | 384 |
| Val | Arg | Ala | Thr | Leu | Gly | Ser | Gln | Thr | Ser | Ala | Trp | Ser | Ile | Leu | Lys | |
| | | 115 | | | | | 120 | | | | | 125 | | | | |
| cat | ccc | ttt | aat | aga | aac | tca | acc | atc | ctt | acc | cga | cct | ggg | atg | gag | 432 |
| His | Pro | Phe | Asn | Arg | Asn | Ser | Thr | Ile | Leu | Thr | Arg | Pro | Gly | Met | Glu | |
| | 130 | | | | | 135 | | | | | 140 | | | | | |
| atc | acc | aaa | gat | ggc | ttc | cac | ctg | gtt | att | gag | ctg | gag | gac | ctg | ggg | 480 |
| Ile | Thr | Lys | Asp | Gly | Phe | His | Leu | Val | Ile | Glu | Leu | Glu | Asp | Leu | Gly | |
| 145 | | | | | 150 | | | | | 155 | | | | | 160 | |
| ccc | cag | ttt | gag | ttc | ctt | gtg | gcc | tac | tgg | agg | agg | gag | cct | ggt | gcc | 528 |
| Pro | Gln | Phe | Glu | Phe | Leu | Val | Ala | Tyr | Trp | Arg | Arg | Glu | Pro | Gly | Ala | |
| | | | | 165 | | | | | 170 | | | | | 175 | | |
| gag | gaa | cat | gtc | aaa | atg | gtg | agg | agt | ggg | ggt | att | cca | gtg | cac | cta | 576 |
| Glu | Glu | His | Val | Lys | Met | Val | Arg | Ser | Gly | Gly | Ile | Pro | Val | His | Leu | |
| | | | 180 | | | | | 185 | | | | | 190 | | | |
| gaa | acc | atg | gag | cca | ggg | gct | gca | tac | tgt | gtg | aag | gcc | cag | aca | ttc | 624 |
| Glu | Thr | Met | Glu | Pro | Gly | Ala | Ala | Tyr | Cys | Val | Lys | Ala | Gln | Thr | Phe | |
| | | 195 | | | | | 200 | | | | | 205 | | | | |
| gtg | aag | gcc | att | ggg | agg | tac | agc | gcc | ttc | agc | cag | aca | gaa | tgt | gtg | 672 |
| Val | Lys | Ala | Ile | Gly | Arg | Tyr | Ser | Ala | Phe | Ser | Gln | Thr | Glu | Cys | Val | |
| | 210 | | | | | 215 | | | | | 220 | | | | | |
| gag | gtg | caa | gga | gag | gcc | act | gtg | gct | gca | cca | tct | gtc | ttc | atc | ttc | 720 |
| Glu | Val | Gln | Gly | Glu | Ala | Thr | Val | Ala | Ala | Pro | Ser | Val | Phe | Ile | Phe | |
| 225 | | | | | 230 | | | | | 235 | | | | | 240 | |
| ccg | cca | tct | gat | gag | cag | ttg | aaa | tct | ggt | acc | gcc | tct | gtt | gtg | tgc | 768 |
| Pro | Pro | Ser | Asp | Glu | Gln | Leu | Lys | Ser | Gly | Thr | Ala | Ser | Val | Val | Cys | |
| | | | | 245 | | | | | 250 | | | | | 255 | | |

```
ctg ctg aat aac ttc tat ccc aga gag gcc aaa gta cag tgg aag gtg      816
Leu Leu Asn Asn Phe Tyr Pro Arg Glu Ala Lys Val Gln Trp Lys Val
        260                 265                 270 gat aac gcc ctc caa tcg ggt aac tcc cag gag agt gtc aca gag cag      864
Asp Asn Ala Leu Gln Ser Gly Asn Ser Gln Glu Ser Val Thr Glu Gln
    275                 280                 285 gac agc aag gac agc acc tac agc ctc agc agc acc ctg acg ctg agc      912
Asp Ser Lys Asp Ser Thr Tyr Ser Leu Ser Ser Thr Leu Thr Leu Ser
290                 295                 300 aaa gca gac tac gag aaa cac aaa gtc tac gcc tgc gaa gtc acc cat      960
Lys Ala Asp Tyr Glu Lys His Lys Val Tyr Ala Cys Glu Val Thr His
305                 310                 315                 320 cag ggc ctg agc tcg ccc gtc aca aag agc ttc aac agg gga gag tgt     1008
Gln Gly Leu Ser Ser Pro Val Thr Lys Ser Phe Asn Arg Gly Glu Cys
                325                 330                 335 tag                                                                 1011

<210> SEQ ID NO 34
<211> LENGTH: 336
<212> TYPE: PRT
<213> ORGANISM: Homo sapiens

<400> SEQUENCE: 34

Met Gln Thr Phe Thr Met Val Leu Glu Glu Ile Trp Thr Ser Leu Phe
 1                5                  10                  15

Met Trp Phe Phe Tyr Ala Leu Ile Pro Cys Leu Leu Thr Asp Glu Val
                20                  25                  30

Ala Ile Leu Pro Ala Pro Gln Asn Leu Ser Val Leu Ser Thr Asn Met
            35                  40                  45

Lys His Leu Leu Met Trp Ser Pro Val Ile Ala Pro Gly Glu Thr Val
        50                  55                  60

Tyr Tyr Ser Val Glu Tyr Gln Gly Glu Tyr Glu Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Thr Val Ala Ala Pro Ser Val Phe Ile Phe
225                 230                 235                 240

Pro Pro Ser Asp Glu Gln Leu Lys Ser Gly Thr Ala Ser Val Val Cys
                245                 250                 255
```

```
Leu Leu Asn Asn Phe Tyr Pro Arg Glu Ala Lys Val Gln Trp Lys Val
            260                 265                 270

Asp Asn Ala Leu Gln Ser Gly Asn Ser Gln Glu Ser Val Thr Glu Gln
        275                 280                 285

Asp Ser Lys Asp Ser Thr Tyr Ser Leu Ser Ser Thr Leu Thr Leu Ser
    290                 295                 300

Lys Ala Asp Tyr Glu Lys His Lys Val Tyr Ala Cys Glu Val Thr His
305                 310                 315                 320

Gln Gly Leu Ser Ser Pro Val Thr Lys Ser Phe Asn Arg Gly Glu Cys
                325                 330                 335

<210> SEQ ID NO 35
<211> LENGTH: 38
<212> TYPE: DNA
<213> ORGANISM: Homo sapiens

<400> SEQUENCE: 35
tcagtcggaa ttcgcagaag ccatgcgggc tcccggcc                         38

<210> SEQ ID NO 36
<211> LENGTH: 35
<212> TYPE: DNA
<213> ORGANISM: Homo sapiens

<400> SEQUENCE: 36
ctgtgacgct agcctctgat gattgatctt tcaaa                            35

<210> SEQ ID NO 37
<211> LENGTH: 43
<212> TYPE: DNA
<213> ORGANISM: Homo sapiens

<400> SEQUENCE: 37
gatgtctgaa ttcgcagaag ccatgcagac tttcacaatg gtt                   43

<210> SEQ ID NO 38
<211> LENGTH: 86
<212> TYPE: DNA
<213> ORGANISM: Homo sapiens

<400> SEQUENCE: 38
aagacggtac cagatttcaa ctgctcatca gatggcggga agatgaagac agatggtgca  60
gccacagtgg cctctccttg cacctc                                      86

<210> SEQ ID NO 39
<211> LENGTH: 559
<212> TYPE: PRT
<213> ORGANISM: Homo sapiens

<400> SEQUENCE: 39

Val Pro Cys Val Ser Gly Gly Leu Pro Lys Pro Ala Asn Ile Thr Phe
1               5                   10                  15

Leu Ser Ile Asn Met Lys Asn Val Leu Gln Trp Thr Pro Pro Glu Gly
            20                  25                  30

Leu Gln Gly Val Lys Val Thr Tyr Thr Val Gln Tyr Phe Ile Tyr Gly
        35                  40                  45

Gln Lys Lys Trp Leu Asn Lys Ser Glu Cys Arg Asn Ile Asn Arg Thr
    50                  55                  60

Tyr Cys Asp Leu Ser Ala Glu Thr Ser Asp Tyr Glu His Gln Tyr Tyr
65                  70                  75                  80
```

-continued

```
Ala Lys Val Lys Ala Ile Trp Gly Thr Lys Cys Ser Lys Trp Ala Glu
                85                  90                  95

Ser Gly Arg Phe Tyr Pro Phe Leu Glu Thr Gln Ile Gly Pro Pro Glu
            100                 105                 110

Val Ala Leu Thr Thr Asp Glu Lys Ser Ile Ser Val Val Leu Thr Ala
        115                 120                 125

Pro Glu Lys Trp Lys Arg Asn Pro Glu Asp Leu Pro Val Ser Met Gln
    130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
        195                 200                 205

Arg Thr Leu Lys Asp Gln Gly Gly Gly Ser Gly Gly Gly Gly Ser
    210                 215                 220

Gly Gly Gly Gly Ser Ala Ser Thr Lys Gly Pro Ser Val Phe Pro Leu
225                 230                 235                 240

Ala Pro Ser Ser Lys Ser Thr Ser Gly Gly Thr Ala Ala Leu Gly Cys
                245                 250                 255

Leu Val Lys Asp Tyr Phe Pro Glu Pro Val Thr Val Ser Trp Asn Ser
            260                 265                 270

Gly Ala Leu Thr Ser Gly Val His Thr Phe Pro Ala Val Leu Gln Ser
        275                 280                 285

Ser Gly Leu Tyr Ser Leu Ser Ser Val Val Thr Val Pro Ser Ser Ser
    290                 295                 300

Leu Gly Thr Gln Thr Tyr Ile Cys Asn Val Asn His Lys Pro Ser Asn
305                 310                 315                 320

Thr Lys Val Asp Lys Lys Val Glu Pro Lys Ser Cys Asp Lys Thr His
                325                 330                 335

Thr Cys Pro Pro Cys Pro Ala Pro Glu Ala Glu Gly Ala Pro Ser Val
            340                 345                 350

Phe Leu Phe Pro Pro Lys Pro Lys Asp Thr Leu Met Ile Ser Arg Thr
        355                 360                 365

Pro Glu Val Thr Cys Val Val Val Asp Val Ser His Glu Asp Pro Glu
    370                 375                 380

Val Lys Phe Asn Trp Tyr Val Asp Gly Val Glu Val His Asn Ala Lys
385                 390                 395                 400

Thr Lys Pro Arg Glu Glu Gln Tyr Asn Ser Thr Tyr Arg Val Val Ser
                405                 410                 415

Val Leu Thr Val Leu His Gln Asp Trp Leu Asn Gly Lys Glu Tyr Lys
            420                 425                 430

Cys Lys Val Ser Asn Lys Ala Leu Pro Ser Ser Ile Glu Lys Thr Ile
        435                 440                 445

Ser Lys Ala Lys Gly Gln Pro Arg Glu Pro Gln Val Tyr Thr Leu Pro
    450                 455                 460

Pro Ser Arg Asp Glu Leu Thr Lys Asn Gln Val Ser Leu Thr Cys Leu
465                 470                 475                 480

Val Lys Gly Phe Tyr Pro Ser Asp Ile Ala Val Glu Trp Glu Ser Asn
                485                 490                 495
```

```
Gly Gln Pro Glu Asn Asn Tyr Lys Thr Thr Pro Pro Val Leu Asp Ser
                500                 505                 510

Asp Gly Ser Phe Phe Leu Tyr Ser Lys Leu Thr Val Asp Lys Ser Arg
            515                 520                 525

Trp Gln Gln Gly Asn Val Phe Ser Cys Ser Val Met His Glu Ala Leu
        530                 535                 540

His Asn His Tyr Thr Gln Lys Ser Leu Ser Leu Ser Pro Gly Lys
545                 550                 555

<210> SEQ ID NO 40
<211> LENGTH: 547
<212> TYPE: PRT
<213> ORGANISM: Homo sapiens

<400> SEQUENCE: 40

Val Pro Cys Val Ser Gly Gly Leu Pro Lys Pro Ala Asn Ile Thr Phe
1               5                   10                  15

Leu Ser Ile Asn Met Lys Asn Val Leu Gln Trp Thr Pro Pro Glu Gly
            20                  25                  30

Leu Gln Gly Val Lys Val Thr Tyr Thr Val Gln Tyr Phe Ile Tyr Gly
        35                  40                  45

Gln Lys Lys Trp Leu Asn Lys Ser Glu Cys Arg Asn Ile Asn Arg Thr
    50                  55                  60

Tyr Cys Asp Leu Ser Ala Glu Thr Ser Asp Tyr Glu His Gln Tyr Tyr
65                  70                  75                  80

Ala Lys Val Lys Ala Ile Trp Gly Thr Lys Cys Ser Lys Trp Ala Glu
                85                  90                  95

Ser Gly Arg Phe Tyr Pro Phe Leu Glu Thr Gln Ile Gly Pro Pro Glu
            100                 105                 110

Val Ala Leu Thr Thr Asp Glu Lys Ser Ile Ser Val Val Leu Thr Ala
        115                 120                 125

Pro Glu Lys Trp Lys Arg Asn Pro Glu Asp Leu Pro Val Ser Met Gln
    130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
        195                 200                 205

Arg Thr Leu Lys Asp Gln Ser Ser Glu Ala Ser Thr Lys Gly Pro Ser
    210                 215                 220

Val Phe Pro Leu Ala Pro Ser Ser Lys Ser Thr Ser Gly Gly Thr Ala
225                 230                 235                 240

Ala Leu Gly Cys Leu Val Lys Asp Tyr Phe Pro Glu Pro Val Thr Val
                245                 250                 255

Ser Trp Asn Ser Gly Ala Leu Thr Ser Gly Val His Thr Phe Pro Ala
            260                 265                 270

Val Leu Gln Ser Ser Gly Leu Tyr Ser Leu Ser Ser Val Val Thr Val
        275                 280                 285

Pro Ser Ser Ser Leu Gly Thr Gln Thr Tyr Ile Cys Asn Val Asn His
    290                 295                 300

Lys Pro Ser Asn Thr Lys Val Asp Lys Lys Val Glu Pro Lys Ser Cys
305                 310                 315                 320
```

```
Asp Lys Thr His Thr Cys Pro Pro Cys Pro Ala Pro Glu Leu Leu Gly
            325                 330                 335

Gly Pro Ser Val Phe Leu Phe Pro Pro Lys Pro Lys Asp Thr Leu Met
            340                 345                 350

Ile Ser Arg Thr Pro Glu Val Thr Cys Val Val Val Asp Val Ser His
            355                 360                 365

Glu Asp Pro Glu Val Lys Phe Asn Trp Tyr Val Asp Gly Val Glu Val
370                 375                 380

His Asn Ala Lys Thr Lys Pro Arg Glu Glu Gln Tyr Asn Ser Thr Tyr
385                 390                 395                 400

Arg Val Val Ser Val Leu Thr Val Leu His Gln Asp Trp Leu Asn Gly
            405                 410                 415

Lys Glu Tyr Lys Cys Lys Val Ser Asn Lys Ala Leu Pro Ala Pro Ile
            420                 425                 430

Glu Lys Thr Ile Ser Lys Ala Lys Gly Gln Pro Arg Glu Pro Gln Val
            435                 440                 445

Tyr Thr Leu Pro Pro Ser Arg Asp Glu Leu Thr Lys Asn Gln Val Ser
            450                 455                 460

Leu Thr Cys Leu Val Lys Gly Phe Tyr Pro Ser Asp Ile Ala Val Glu
465                 470                 475                 480

Trp Glu Ser Asn Gly Gln Pro Glu Asn Asn Tyr Lys Thr Thr Pro Pro
            485                 490                 495

Val Leu Asp Ser Asp Gly Ser Phe Phe Leu Tyr Ser Lys Leu Thr Val
            500                 505                 510

Asp Lys Ser Arg Trp Gln Gln Gly Asn Val Phe Ser Cys Ser Val Met
            515                 520                 525

His Glu Ala Leu His Asn His Tyr Thr Gln Lys Ser Leu Ser Leu Ser
            530                 535                 540

Pro Gly Lys
545

<210> SEQ ID NO 41
<211> LENGTH: 323
<212> TYPE: PRT
<213> ORGANISM: Homo sapiens

<400> SEQUENCE: 41

Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
            35                  40                  45

Tyr Thr Ser His Ile Trp Ile Pro Ser Ser Trp Cys Ser Leu Thr Glu
50                  55                  60

Gly Pro Glu Cys Asp Val Thr Asp Asp Ile Thr Ala Thr Val Pro Tyr
65                  70                  75                  80

Asn Leu Arg Val Arg Ala Thr Leu Gly Ser Gln Thr Ser Ala Trp Ser
            85                  90                  95

Ile Leu Lys His Pro Phe Asn Arg Asn Ser Thr Ile Leu Thr Arg Pro
            100                 105                 110

Gly Met Glu Ile Pro Lys His Gly Phe His Leu Val Ile Glu Leu Glu
            115                 120                 125

Asp Leu Gly Pro Gln Phe Glu Phe Leu Val Ala Tyr Trp Thr Arg Glu
```

-continued

```
            130                 135                 140
Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                    165                 170                 175

Gln Thr Phe Val Lys Ala Ile Gly Arg Tyr Ser Ala Phe Ser Gln Thr
                180                 185                 190

Glu Cys Val Glu Val Gln Gly Glu Ala Gly Gly Gly Ser Gly Gly
            195                 200                 205

Gly Gly Ser Gly Gly Gly Ser Arg Thr Val Ala Ala Pro Ser Val
210                 215                 220

Phe Ile Phe Pro Pro Ser Asp Glu Gln Leu Lys Ser Gly Thr Ala Ser
225                 230                 235                 240

Val Val Cys Leu Leu Asn Asn Phe Tyr Pro Arg Glu Ala Lys Val Gln
                245                 250                 255

Trp Lys Val Asp Asn Ala Leu Gln Ser Gly Asn Ser Gln Glu Ser Val
                260                 265                 270

Thr Glu Gln Asp Ser Lys Asp Ser Thr Tyr Ser Leu Ser Ser Thr Leu
            275                 280                 285

Thr Leu Ser Lys Ala Asp Tyr Glu Lys His Lys Val Tyr Ala Cys Glu
        290                 295                 300

Val Thr His Gln Gly Leu Ser Ser Pro Val Thr Lys Ser Phe Asn Arg
305                 310                 315                 320

Gly Glu Cys
```

<210> SEQ ID NO 42
<211> LENGTH: 307
<212> TYPE: PRT
<213> ORGANISM: Homo sapiens

<400> SEQUENCE: 42

```
Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
                20                  25                  30

Glu Thr Val Tyr Tyr Ser Val Glu Tyr Gln Gly Glu Tyr Glu Ser Leu
            35                  40                  45

Tyr Thr Ser His Ile Trp Ile Pro Ser Ser Trp Cys Ser Leu Thr Glu
        50                  55                  60

Gly Pro Glu Cys Asp Val Thr Asp Asp Ile Thr Ala Thr Val Pro Tyr
65                  70                  75                  80

Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
                100                 105                 110

Gly Met Glu Ile Thr Lys Asp Gly Phe His Leu Val Ile Glu Leu Glu
            115                 120                 125

Asp Leu Gly Pro Gln Phe Glu Phe Leu Val Ala Tyr Trp Arg Arg Glu
        130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
                180                 185                 190
```

-continued

```
                180             185             190
Glu Cys Val Glu Val Gln Gly Glu Ala Thr Val Ala Ala Pro Ser Val
        195             200             205

Phe Ile Phe Pro Pro Ser Asp Glu Gln Leu Lys Ser Gly Thr Ala Ser
        210             215             220

Val Val Cys Leu Leu Asn Asn Phe Tyr Pro Arg Glu Ala Lys Val Gln
225             230             235             240

Trp Lys Val Asp Asn Ala Leu Gln Ser Gly Asn Ser Gln Glu Ser Val
            245             250             255

Thr Glu Gln Asp Ser Lys Asp Ser Thr Tyr Ser Leu Ser Ser Thr Leu
        260             265             270

Thr Leu Ser Lys Ala Asp Tyr Glu Lys His Lys Val Tyr Ala Cys Glu
        275             280             285

Val Thr His Gln Gly Leu Ser Ser Pro Val Thr Lys Ser Phe Asn Arg
    290             295             300

Gly Glu Cys
305
```

… … …

METHOD FOR TREATING INFLAMMATION

This claims the benefit of U.S. Provisional Application No. 60/233,305 filed on Sep. 15, 2000.

BACKGROUND OF THE INVENTION

Inflammation normally is a localized, protective response to trauma or microbial invasion that destroys, dilutes, or walls-off the injurious agent and the injured tissue. It is characterized in the acute form by the classic signs of pain, heat, redness, swelling, and loss of function. Microscopically it involves a complex series of events, including dilation of arterioles, capillaries, and venules, with increased permeability and blood flow, exudation of fluids, including plasma proteins, and leukocyte migration into the area of inflammation.

Diseases characterized by inflammation are significant causes of morbidity and mortality in humans. Commonly, inflammation occurs as a defensive response to invasion of the host by foreign, particularly microbial, material. Responses to mechanical trauma, toxins, and neoplasia also may results in inflammatory reactions. The accumulation and subsequent activation of leukocytes are central events in the pathogenesis of most forms of inflammation. Deficiencies of inflammation compromise the host. Excessive inflammation caused by abnormal recognition of host tissue as foreign or prolongation of the inflammatory process may lead to inflammatory diseases as diverse as diabetes, atherosclerosis, cataracts, reperfusion injury, and cancer, to post-infectious syndromes such as in infectious meningitis, rheumatic fever, and to rheumatic diseases such as systemic lupus erythematosus and rheumatoid arthritis. The centrality of the inflammatory response in these varied disease processes makes its regulation a major element in the prevention control or cure of human disease. Important cytokines in the inflammatory process are IL-19, U.S. Pat. No. 5,985,614 and mda7, Jiang, H., et al.*Oncogene* 10: 2477-2486 (1995). Thus, there is a need to produce agents that would inhibit inflammation related to one or more of the above-mentioned inflammatory-related proteins.

DESCRIPTION OF THE INVENTION

Accordingly, the present invention fills this need by providing for a method for treating inflammation, comprising administering to a mammal in need of treatment of inflammation a soluble IL-20RA/IL-20RBreceptor that binds to IL-19 or mda7.

The teachings of all the references cited herein are incorporated in their entirety by reference.

Definitions

Prior to setting forth the invention in detail, it may be helpful to the understanding thereof to define the following terms.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A, Nilsson et al., *EMBO J.* 4:1075 (1985); Nilsson et al., *Methods Enzymol.* 198:3 (1991), glutathione S transferase, Smith and Johnson, *Gene* 67:31 (1988), Glu-Glu affinity tag, Grussenmeyer et al., *Proc. Natl. Acad. Sci. USA* 82:7952-4 (1985), substance P, Flag™ peptide, Hopp et al., *Biotechnology* 6:1204-1210 (1988), streptavidin binding peptide, or other antigenic epitope or binding domain. See, in general, Ford et al., *Protein Expression and Purification* 2: 95-107 (1991). DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

"Angiogenic" denotes the ability of a compound to stimulate the formation of new blood vessels from existing vessels, acting alone or in concert with one or more additional compounds. Angiogenic activity is measurable as endothelial cell activation, stimulation of protease secretion by endothelial cells, endothelial cell migration, capillary sprout formation, and endothelial cell proliferation.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCTTgagtct-3' and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774-78 (1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, a-globin, b-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

A receptor has been discovered that binds to both IL-19 and mda7 and is a heterodimer comprised of the polypeptide termed 'interleukin-20 receptor alpha IL-20RA' and a polypeptide termed interleukin-20 receptor beta 'IL-20RB'. The IL-20RA polypeptide, nucleic acid that encodes it, antibodies to IL-20RA and methods for producing it are disclosed in U.S. Pat. No. 5,945,511 issued Aug. 31, 1999. SEQ ID NOs: 1-3 are the polynucleotides and polypeptides of IL-20RA. The mature extracellular sequence of IL-20RA is comprised of SEQ ID NO: 3. The IL-20RB polypeptide, nucleic acid that encodes it, antibodies to IL-20RB and methods for producing it are disclosed in International Patent Application No. PCT/US99/03735 (publication no. WO 99/46379) filed on Mar. 8, 1999. A variant of IL-20RB (hereinafter referred to as V-IL-20RB has been cloned and is defined by SEQ ID NOs: 4-6, SEQ ID NO: 6 being the extracellular domain.

Preparation of a Soluble IL-20 Heterodimeric Receptor 'IL-20RA/IL-20RB'

The soluble heterodimeric receptor is comprised of SEQ ID NO: 3 (hereinafter referred to as IL-20RA) and the extracellular domain of IL-20RB or the extracellular domain of a variant of IL-20RB (vIL-20RB, SEQ ID NOs: 4-6) SEQ ID NO: 6. Preferably, the extracellular domain of the IL-20RA polypeptide and the extracellular domain of the IL-20RB polypeptide are covalently bonded together. In a preferred embodiment the one polypeptide has constant region of a heavy chain of an immunoglobulin fused to its carboxy terminus and the other polypeptide has a constant light chain of an immunoglobulin (Ig) fused to its carboxy terminus such that the two polypeptides come together and a disulfide bond is formed between the heavy and the light chains to form a heterodimer. In another method, a peptide linker could be fused to the two carboxy termini of the polypeptides to form a covalently bonded heterodimer.

A method is also provided for producing soluble dimerized extracellular domains of IL-20RA and IL-20RB comprising (a) introducing into a host cell a first DNA sequence comprised of a transcriptional promoter operatively linked to a first secretory signal sequence followed downstream by and in proper reading frame the DNA that encodes the extracellular portion of IL-20RA and the DNA that encodes an immunoglobulin light chain constant region; (b) introducing into the host cell a second DNA construct comprised of a transcriptional promoter operatively linked to a second secretory signal followed downstream by and in proper reading frame a DNA sequence that encodes the extracellular portion of IL-20RB and a DNA sequence that encodes an immunoglobulin heavy chain constant region domain selected from the group consisting of $C_H1$, $C_H2$, $C_H3$ and $C_H4$; (c) growing the host cell in an appropriate growth medium under physiological conditions to allow the secretion of a dimerized heterodimeric fusion protein comprised of the extracellular domain of IL-20RA? and IL-20RB; and (d) isolating the dimerized polypeptide from the host cell. In one embodiment, the second DNA sequence further encodes an immunoglobulin heavy chain hinge region wherein the hinge region is joined to the heavy chain constant region domain. In another embodiment, the second DNA sequence further encodes an immunoglobulin variable region joined upstream of and in proper reading frame with the immunoglobulin heavy chain constant region.

In an alternative embodiment a method is provided for producing soluble dimerized extracellular domains of IL-20RA and IL-20RB comprising (a) introducing into a host cell a first DNA sequence comprised of a transcriptional promoter operatively linked to a first secretory signal sequence followed downstream by and in proper reading frame the DNA that encodes the extracellular portion of IL-20RB and the DNA that encodes an immunoglobulin light chain constant region; (b) introducing into the host cell a second DNA construct comprised of a transcriptional promoter operatively linked to a second secretory signal followed downstream by and in proper reading frame a DNA sequence that encodes the extracellular portion of IL-20RA and a DNA sequence that encodes an immunoglobulin heavy chain constant region domain selected from the group consisting of $C_H1$, $C_H2$, $C_H3$ and $C_H4$; (c) growing the host cell in an appropriate growth medium under physiological conditions to allow the secretion of a dimerized heterodimeric fusion protein comprised of the extracellular domain of IL-20RA and IL-20RB; and (d) isolating the dimerized polypeptide from the host cell. In one embodiment, the second DNA sequence further encodes an immunoglobulin heavy chain hinge region wherein the hinge region is joined to the heavy chain constant region domain. In another embodiment, the second DNA sequence further encodes an immunoglobulin variable region joined upstream of and in proper reading frame with the immunoglobulin heavy chain constant region. (See U.S. Pat. No. 5,843,725.)

Polynucleotides

Generally, a cDNA sequence encodes the described polypeptides herein. A cDNA sequence that encodes a polypeptide of the present invention is comprised of a series of codons, each amino acid residue of the polypeptide being encoded by a codon and each codon being comprised of three nucleotides. The amino acid residues are encoded by their respective codons as follows.

Alanine (Ala) is encoded by GCA, GCC, GCG or GCT;
Cysteine (Cys) is encoded by TGC or TGT;
Aspartic acid (Asp) is encoded by GAC or GAT;
Glutamic acid (Glu) is encoded by GAA or GAG;
Phenylalanine (Phe) is encoded by TTC or TTT;
Glycine (Gly) is encoded by GGA, GGC, GGG or GGT;
Histidine (His) is encoded by CAC or CAT;
Isoleucine (Ile) is encoded by ATA, ATC or ATT;
Lysine (Lys) is encoded by AAA, or AAG;
Leucine (Leu) is encoded by TTA, TTG, CTA, CTC, CTG or CTT;
Methionine (Met) is encoded by ATG;
Asparagine (Asn) is encoded by AAC or AAT;
Proline (Pro) is encoded by CCA, CCC, CCG or CCT;
Glutamine (Gln) is encoded by CAA or CAG;
Arginine (Arg) is encoded by AGA, AGG, CGA, CGC, CGG or CGT;
Serine (Ser) is encoded by AGC, AGT, TCA, TCC, TCG or TCT;
Threonine (Thr) is encoded by ACA, ACC, ACG or ACT;
Valine (Val) is encoded by GTA, GTC, GTG or GTT;
Tryptophan (Trp) is encoded by TGG; and
Tyrosine (Tyr) is encoded by TAC or TAT.

Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722 (1991); Ellman et al., *Methods Enzymol.* 202:301 (1991; Chung et al., *Science* 259:806-809 (1993); and Chung et al., *Proc. Natl. Acad. Sci. USA* 90:10145-1019 (1993). In a second method, translation is carried out in Xenopus oocytes by microinjection of mutated mRNA and chemically aminoacylated suppressor tRNAs, Turcatti et al., *J. Biol. Chem.* 271:19991-19998 (1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-7476 (1994). Naturally occurring amino acid residues can be converted to non-naturally occurring species by in vitro chemical modification. Chemical modification can be combined with site-directed mutagenesis to further expand the range of substitutions, Wynn and Richards, *Protein Sci.* 2:395-403 (1993).

A limited number of non-conservative amino acids, amino acids that are not encoded by the genetic code, non-naturally occurring amino acids, and unnatural amino acids may be substituted for amino acid residues.

Essential amino acids in the polypeptides of the present invention can be identified according to procedures known in the art, such as site-directed mutagenesis or alanine-scanning mutagenesis, Cunningham and Wells, *Science* 244: 1081-1085 (1989); Bass et al., *Proc. Natl. Acad. Sci. USA* 88:4498-502 (1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699-708, 1996. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-312 (1992); Smith et al., *J. Mol. Biol.* 224: 899-904 (1992); Wlodaver et al., *FEBS Lett.* 309:59-64 (1992).

Multiple amino acid substitutions can be made and tested using known methods of mutagenesis and screening, such as those disclosed by Reidhaar-Olson and Sauer, *Science* 241: 53-57 (1988) or Bowie and Sauer, *Proc. Natl. Acad. Sci. USA* 86:2152-2156 (1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display, e.g., Lowman et al., *Biochem.* 30:10832-10837 (1991); Ladner et al., U.S. Pat. No. 5,223,409; Huse, WIPO Publication WO 92/06204) and region-directed mutagenesis, Derbyshire et al., *Gene* 46:145 (1986); Ner et al., *DNA* 7:127 (1988).

Variants of the disclosed IL-20RA and IL-20RB DNA and polypeptide sequences can be generated through DNA shuffling as disclosed by Stemmer, *Nature* 370:389-391, (1994), Stemmer, *Proc. Natl. Acad. Sci. USA* 91:10747-10751 (1994) and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

PROTEIN PRODUCTION

Polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., (Cold Spring Harbor Laboratory Press, Cold Spring Harbor, N.Y., 1989), and Ausubel et al., eds., *Current Protocols in Molecular Biology* (John Wiley and Sons, Inc., N.Y., 1987).

In general, a DNA sequence encoding a polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the native polypeptides, or may be derived from another secreted protein (e.g., t-PA) or synthesized de novo. The secretory signal sequence is operably linked to the DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection, Wigler et al., *Cell* 14:725 (1978); Corsaro and Pearson, *Somatic Cell Genetics* 7:603 (1981); Graham and Van der Eb, *Virology* 52:456 (1973), electroporation, Neumann et al., *EMBO J.* 1:841-845 (1982), DEAE-dextran mediated transfection (Ausubel et al., ibid., and liposome-mediated transfection, Hawley-Nelson et al., *Focus* 15:73 (1993); Ciccarone et al., *Focus* 15:80 (1993), and viral vectors, Miller and Rosman, *BioTechniques* 7:980(1989); Wang and Finer, *Nature Med.* 2:714 (1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59 (1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47 (1987). Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). DNA encoding a polypeptide is inserted into the baculoviral genome in place of the AcNPV polyhedrin gene coding sequence by one of two methods. The first is the traditional method of homologous DNA recombination between wild-type AcNPV and a transfer vector containing the gene flanked by AcNPV sequences. Suitable insect cells, e.g. SF9 cells, are infected with wild-type AcNPV and transfected with a transfer vector comprising a polynucleotide operably linked to an AcNPV polyhedrin gene promoter, terminator, and flanking sequences. See, King, L. A. and Possee, R. D., *The Baculovirus Expression System: A Laboratory Guide*, (Chapman & Hall, London); O'Reilly, D. R. et al., *Baculovirus Expression Vectors: A Laboratory Manual* (Oxford University Press, New York, N.Y., 1994); and, Richardson, C. D., Ed., *Baculovirus Expression Protocols. Methods in Molecular Biology*, (Humana Press, Totowa, N.J. 1995). Natural recombination within an insect cell will result in a recombinant baculovirus that contains coding sequences driven by the polyhedrin promoter. Recombinant viral stocks are made by methods commonly used in the art.

The second method of making recombinant baculovirus utilizes a transposon-based system described by Luckow, V. A, et al., *J Virol* 67:4566 (1993). This system is sold in the Bac-to-Bac kit (Life Technologies, Rockville, Md.). This system utilizes a transfer vector, pFastBac1™ (Life Technologies) containing a Tn7 transposon to move the DNA encoding the polypeptide into a baculovirus genome maintained in *E. coli* as a large plasmid called a "bacmid." The pFastBac1™ transfer vector utilizes the AcNPV polyhedrin promoter to drive the expression of the gene of interest. However, pFastBac1™ can be modified to a considerable degree. The polyhedrin promoter can be removed and substituted with the baculovirus basic protein promoter (also known as Pcor, p6.9 or MP promoter), is expressed earlier in the baculovirus infection, and has been shown to be advantageous for expressing secreted proteins. See, Hill-Perkins, M. S. and Possee, R. D., *J Gen Virol* 71:971 (1990); Bonning, B. C. et al., *J Gen Virol* 75:1551 (1994); and, Chazenbalk, G. D., and Rapoport, B., *J Biol Chem* 270:1543 (1995). In such transfer vector constructs, a short or long version of the basic protein promoter can be used. Moreover, transfer vectors can be constructed that replace the native secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native secretory signal sequence. In addition, transfer vectors can include an in-frame fusion with DNA encoding an epitope tag at the C- or N-terminus of the expressed polypeptide, for example, a Glu-Glu epitope tag, Grussenmeyer, T. et al., *Proc Natl Acad Sci.* 82:7952 (1985). Using a technique known in the art, a transfer vector containing a recombinant gene is transformed into *E. coli*, and screened for bacmids that contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses the polypeptide is subsequently produced. Recombinant viral stocks are made by methods commonly used the art.

The recombinant virus is used to infect host cells, typically a cell line derived from the fall army worm, *Spodoptera frugiperda*. See, in general, Glick and Pasternak, *Molecular Biotechnology: Principles and Applications of Recombinant DNA* (ASM Press, Washington, D.C., 1994). Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2\text{-}5\times10^5$ cells to a density of $1\text{-}2\times10^6$ cells at which time a recombinant viral stock is added at a multiplicity of infection (MOI) of 0.1 to 10, more typically near 3. The recombinant virus-infected cells typically produce the recombinant polypeptide at 12-72 hours post-infection and secrete it with varying efficiency into the medium. The culture is usually harvested 48 hours post-infection. Centrifugation is used to separate the cells from the medium (supernatant). The supernatant containing the polypeptide is filtered through micropore filters, usually 0.45 μm pore size. Procedures used are generally described in available laboratory manuals (King, L. A. and Possee, R. D., ibid.; O'Reilly, D. R. et al., ibid.; Richardson, C. D., ibid.). Subsequent purification of the polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459 (1986) and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (τ) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art, see, e.g., Sambrook et al., ibid.). When expressing a polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient, which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Protein Isolation

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant polypeptides (or chimeric polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods* (Pharmacia LKB Biotechnology, Uppsala, Sweden, 1988).

Polypeptides can be isolated by exploitation of their properties. Proteins that are fused to the Fc constant region of an antibody can be isolated by means of a 'Protein A' column, *Methods in Enzymol.*, Vol. 182, "Guide to Protein Purification", M. Deutscher, (ed.),page 529-539 (Acad. Press, San Diego, 1990). Within additional embodiments of the invention, a fusion of the polypeptide of interest and an affinity tag (e.g., maltose-binding protein, an immunoglobulin domain) may be constructed to facilitate purification.

Moreover, using methods described in the art, polypeptide fusions, or hybrid proteins, are constructed using regions or domains of polypeptides, Sambrook et al., ibid., Altschul et al., ibid., Picard, *Cur. Opin. Biology,* 5:511 (1994). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between a polypeptide of the present invention with the functionally equivalent domain(s) from another family member. Such domains include, but are not limited to, the secretory signal sequence, conserved, and significant domains or regions in this family. Such fusion proteins would be expected to have a biological functional profile that is the same or similar to polypeptides of the present invention or other known family proteins, depending on the fusion constructed. Moreover, such fusion proteins may exhibit other properties as disclosed herein.

The quantity of the IL-20RA/IL-20RB soluble receptor necessary to inhibit IL-19 or mda7 will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in vivo administration of these reagents. Animal testing of effective doses for treatment of particular disorders will provide further predictive indication of human dosage. Methods for administration include oral, intravenous, peritoneal, intramuscular, transdermal or administration into the lung or trachea in spray form by means or a nebulizer or atomizer. Pharmaceutically acceptable carriers will include water, saline, buffers to name just a few. Dosage ranges would ordinarily be expected from 1 82 g to 1000 µg per kilogram of body weight per day. However, the doses may be higher or lower as can be determined by a medical doctor with ordinary skill in the art. For a complete discussion of drug formulations and dosage ranges see *Remington's Pharmaceutical Sciences,* 18$^{th}$ Ed., (Mack Publishing Co., Easton, Pa., 1996), and *Goodman and Gilman's: The Pharmacological Bases of Therapeutics,* 9$^{th}$ Ed. (Pergamon Press 1996).

The invention is further illustrated by the following non-limiting examples.

EXAMPLE 1

Cloning of IL-20RB Variant

1. IL-20RB

Two novel members of the class II cytokine receptor family were described in International Patent Application No. PCT/US99/03735 filed Mar. 8, 1999. IL-20RB shares 31% sequence homology with class II cytokine receptor IL-20RA, U.S. Pat. No. 5,945,511 issued Aug. 31, 1999. IL-20 is a homologue of IL-10, which is a member of class II cytokine family. The fact that IL-20RB is a class II cytokine receptor and is expressed in fetal liver, fetal small intestine, fetal ovary, normal skin and psoriasis skin made IL-20RB a plausible candidate for an IL-20 receptor subunit.

2. Cloning of IL-20RB Coding Region

Two PCR primers were designed based on the sequence from International Patent Application No. PCT/US99/03735 (publication no. WO 99/46379) filed on Mar. 8, 1999: ZC25480 (SEQ ID NO: 7) contains the ATG (Met1) codon with an EcoRI restriction site, ZC25481 (SEQ ID NO: 8) contains the stop codon (TAG) with a XhoI restriction site. The PCR amplification was carried out using a human keratinocyte (HaCaT) cDNA library DNA as a template and ZC25480 (SEQ ID NO: 7) and ZC25481 (SEQ ID NO: 8) as primers. The PCR reaction was performed as follows: incubation at 94° C. for 1 min followed by 30 cycles of 94° C. for 30 sec and 68° C. for 2 min, after additional 68° C. for 4 min, the reaction was stored at 4° C. The PCR products were run on 1% Agarose gel, and a 1 kb DNA band was observed. The PCR products were cut from the gel and the DNA was purified using a QIAquick Gel Extraction Kit (Qiagen). The purified DNA was digested with EcoRI and XhoI, and cloned into a pZP vector that was called pZP7N. A pZP plasmid is a mammalian expression vector containing an expression cassette having the mouse metallothionein-1 promoter, human tPA leader peptide, multiple restriction sites for insertion of coding sequences, a Glu-Glu tag, and a human growth hormone terminator. The plasmid also has an *E. coli* origin of replication, a mammalian selectable marker expression unit having an SV40 promoter, an enhancer and an origin of replication, as well as a DHFR gene, and the SV40 terminator. Several IL-20R?-pZP7N clones were sequenced. They all contain three non-conservative mutations compared with the patent sequence of IL-20RB? in PCT/US99/03735: (sequence IL-20R?-pZP7N), 146 Pro (CCC)—Thr (ACC), 148 His (CAT)—Asp (GAT), and 171 Thr (ACG)—Arg (AGG).

To verify the three substitutions in IL-20R?-pZP7N clone, PCR amplification was carried out using three difference cDNA sources—fetal skin marathon cDNA, HaCaT cDNA library DNA, and prostate smooth muscle cDNA library DNA—as templates. The PCR products were gel purified and sequenced. The sequence of each of the three PCR products was consistent with that of the IL-20R?-pZP7N clone.

EXAMPLE 2

IL-20RA Receptor-Ig Fusion Protein

The expression vector pEZE3 was used to express the recombinant IL-20 receptor-Ig fusion protein. pEZE3 is derived from pDC312. pDC312 was obtained through license from Immunex Corporation. pDC312 and pEZE3 contain an EASE segment as described in WO 97/25420. The presence of the EASE segment in an expression vector can improve expression of recombinant proteins two to eight fold in stable cell pools.

pEZE3 is a tricistronic expression vector that may be used to express up to three different proteins in mammalian cells, preferably Chinese Hamster Ovary (CHO) cells. The pEZE3 expression unit contains the CMV enhancer/promoter, the adenovirus tripartite leader sequence, a multiple cloning site for insertion of the coding region for the first recombinant protein, the poliovirus type 2 internal ribosome entry site, a second multiple cloning site for insertion of the coding region for the second recombinant protein, an encephalomyocarditis virus internal ribosome entry site, a coding segment for mouse dihydrofolate reductase, and the SV40 transcription terminator. In addition, pEZE3 contains an *E. coli* origin of replication and the bacterial beta lactamase gene.

The IL-20 receptor-Ig fusion protein is a disulfide linked heterotetramer consisting of two chains of the extracellular domain of the human fused to the wild type human immunoglobulin kappa light chain constant region and two chains of the human IL-20R protein extracellular domain fused to a mutated human immunoglobulin gamma 1 constant region. The human immunoglobulin gamma 1 constant region contains amino acid substitutions to reduce FcRI binding and C1q complement fixation.

The human IL-20RB extracellular domain human immunoglobulin kappa light chain constant region fusion construct was generated by overlap PCR. The IL-20RB coding segment consists of amino acids 1 to 230. The template used for the PCR amplification of the IL-20R segment was a previously generated IL-20RB human kappa light chain constant region expression construct. Oligonucleotide primers SEQ ID NO: 9 (zc27,522) and SEQ ID NO: 10 (zc27,684) were used to amplify the IL-20RB segment. The entire wild type human immunoglobulin kappa light chain constant region was used. The template used for the PCR amplification of the wild type human immunoglobulin kappa light chain constant region segment was a previously generated IL-20RB human kappa light chain constant region expression construct. Oligonucleotide primers SEQ ID NO: 11 (zc27,675) and SEQ ID NO: 12 (zc27,685) were used to amplify the wild type human immunoglobulin kappa light chain constant region. The two protein coding domains were linked by overlap PCR using oligonucleotides SEQ ID NO: 9 (zc27,522) and SEQ ID NO: 12 (zc27,685). A $(Gly_4Ser)_3$ peptide linker was inserted between the two protein domains. The $(Gly_4Ser)_3$ peptide linker was encoded on the PCR primers SEQ ID NO: 11 (zc27,675) and SEQ ID NO: 10 (zc27,684).

The human IL-20RA extracellular domain human immunoglobulin gamma 1 heavy chain constant region fusion construct was generated by overlap PCR of four separate DNA fragments, each generated by separate PCR amplification reactions The first fragment contained an optimized tPA (tissue plasminogen activator) signal sequence. The otPA signal sequence was amplified using oligonucleotide primers SEQ ID NO: 13 (zc27,525) and SEQ ID NO: 14 (zc27,526) using an in-house previously generated expression vector as the template.

The second fragment contained the IL-20RA extracellular domain coding region consisting of amino acids 1 to 214. Oligonucleotide primers SEQ ID NO: 15 (zc27,524) and SEQ ID NO: 16 (zc27,674) were used to amplify this IL-20RA? segment using a previously generated clone of IL-20RA as the template.

The human gamma 1 heavy chain constant region was generated from 2 segments. The first segment containing the $C_H1$ domain was amplified using oligonucleotide primers SEQ ID NO: 17 (zc27,676) and SEQ ID NO: 18 (zc28,077) using a clone of the wild type human gamma 1 heavy chain constant region as the template. The second segment containing the remaining hinge, $C_H2$, and $C_H3$ domains of the human immunoglobulin gamma 1 heavy chain constant region was generated by PCR amplification using oligonucleotide primers SEQ ID NO: 19 (zc28,076) and SEQ ID NO: 20 (zc27,523).

The four protein coding domains were linked by overlap PCR using oligonucleotides SEQ ID NO: 13 (zc27,525) and SEQ ID NO: 20 (zc27,523). A $(Gly_4Ser)_3$ peptide linker was inserted between the zcytor7 and CH1 protein domains. The $(Gly_4Ser)_3$ peptide linker was encoded on the PCR primers SEQ ID NO: 17 (zc27,676) and SEQ ID NO: 16 (zc27,674).

The IL-20RB extracellular domain human immunoglobulin kappa light chain constant region fusion coding segment was cloned into the second MCS while the human IL-20RA extracellular domain human immunoglobulin gamma 1 heavy chain constant region fusion coding segment was cloned into the first MCS of pEZE3.

The plasmid was used to transfect CHO cells. The cells were selected in medium without hypoxanthine or thymidine and the transgene was amplified using methotrexate. The presence of protein was assayed by Western blotting using anti human gamma 1 heavy chain constant region and anti human kappa light chain antibodies.

The IL-20RB extracellular domain human immunoglobulin kappa light chain constant region fusion protein and DNA sequence are shown in SEQ ID NOs: 21 and 22.

The IL-20RA extracellular domain human immunoglobulin gamma 1 heavy constant region fusion protein and DNA sequence are shown in SEQ ID NOs: 23 and 24.

EXAMPLE 3

IL-20RA/B Receptor-Ig Fusion Protein

The expression vector pEZE3 was used to express the recombinant IL-20RA/B receptor-Ig fusion protein. pEZE3 is derived from pDC312. pDC312 was obtained through license from Immunex Corporation. pDC312 and pEZE3 contain an EASE segment as described in WO 97/25420. The presence of the EASE segment in an expression vector can improve expression of recombinant proteins two to eight fold in stable cell pools.

pEZE3 is a tricistronic expression vector that may be used to express up to three different proteins in mammalian cells, preferably Chinese Hamster Ovary (CHO) cells. The pEZE3 expression unit contains the CMV enhancer/promoter, the adenovirus tripartite leader sequence, a multiple cloning site for insertion of the coding region for the first recombinant protein, the poliovirus type 2 internal ribosome entry site, a second multiple cloning site for insertion of the coding region for the second recombinant protein, an encephalomyocarditis virus internal ribosome entry site, a coding segment for mouse dihydrofolate reductase, and the SV40 transcription terminator. In addition, pEZE3 contains an E. coli origin of replication and the bacterial beta lactamase gene.

The IL-20RA/B receptor-Ig fusion protein is a disulfide linked heterotetramer consisting of two chains of the human IL-20RB protein extracellular domain fused to the wild type human immunoglobulin kappa light chain constant region and two chains of the human IL-20RA protein extracellular domain fused to a mutated human immunoglobulin gamma 1 constant region. The human immunoglobulin gamma 1 constant region contains amino acid substitutions to reduce Fc?RI binding and C1q complement fixation.

The human IL-20RB extracellular domain human immunoglobulin kappa light chain constant region fusion construct was generated by overlap PCR. The IL-20RB coding segment consists of amino acids 1 to 230. The template used for the PCR amplification of the IL-20RB segment was a previously generated IL-20RB human kappa light chain constant region expression construct. Oligonucleotide primers SEQ ID NO: 9 (zc27,522) and SEQ ID NO: 10 (zc27,684) were used to amplify the IL-20RB segment. The entire wild type human immunoglobulin kappa light chain constant region was used. The template used for the PCR amplification of the wild type human immunoglobulin kappa light chain constant region segment was a previously generated IL-20RB human kappa light chain constant region expression construct. Oligonucleotide primers SEQ ID NO: 11 (zc27,675) and SEQ ID NO: 12 (zc27,685) were used to amplify the wild type human immunoglobulin kappa light chain constant region. The two protein coding domains were linked by overlap PCR using oligonucleotides SEQ ID NO: 9 (zc27,522) and SEQ ID NO: 12 (zc27,685). A $(Gly_4Ser)_3$ peptide linker was inserted between the two protein domains. The $(Gly_4Ser)_3$ peptide linker was encoded on the PCR primers SEQ ID NO: 11 (zc27,675) and SEQ ID NO: 10 (zc27,684).

The human IL-20RA extracellular domain human immunoglobulin gamma 1 heavy chain constant region fusion construct was generated by overlap PCR of four separate DNA fragments, each generated by separate PCR amplification reactions.

The first fragment contained an optimized tPA (tissue plasminogen activator) signal sequence. The otPA signal sequence was amplified using oligonucleotide primers SEQ ID NO: 13 (zc27,525) and SEQ ID NO: 14 (zc27,526) using an in-house previously generated expression vector as the template.

The second fragment contained the IL-20RA extracellular domain coding region consisting of amino acids 1 to 214. Oligonucleotide primers SEQ ID NO: 15 (zc27,524) and SEQ ID NO: 16 (zc27,674) were used to amplify this IL-20RA segment using a previously generated clone of IL-20RA as the template.

The human gamma 1 heavy chain constant region was generated from 2 segments. The first segment containing the $C_H1$ domain was amplified using oligonucleotide primers SEQ ID NO: 17 (zc27,676) and SEQ ID NO: 18 (zc28,077) using a clone of the wild type human gamma 1 heavy chain constant region as the template. The second segment containing the remaining hinge, $C_H2$, and $C_H3$ domains of the human immunoglobulin gamma 1 heavy chain constant region was generated by PCR amplification using oligonucleotide primers SEQ ID NO: 19 (zc28,076) and SEQ ID NO: 20 (zc27,523).

The four protein coding domains were linked by overlap PCR using oligonucleotides SEQ ID NO: 13 (zc27,525) and SEQ ID NO: 20 (zc27,523). A $(Gly_4Ser)_3$ peptide linker was inserted between the zcytor7 and CH1 protein domains. The $(Gly_4Ser)_3$ peptide linker was encoded on the PCR primers SEQ ID NO: 17 (zc27,676) and SEQ ID NO: 16 (zc27,674).

The IL-20RB extracellular domain human immunoglobulin kappa light chain constant region fusion coding segment was cloned into the second MCS while the human IL-20RA extracellular domain human immunoglobulin gamma 1 heavy chain constant region fusion coding segment was cloned into the first MCS of pEZE3.

The plasmid was used to transfect CHO cells. The cells were selected in medium without hypoxanthine or thymidine and the transgene was amplified using methotrexate. The presence of protein was assayed by Western blotting using anti human gamma 1 heavy chain constant region and anti human kappa light chain antibodies.

The IL-20RB extracellular domain human immunoglobulin kappa light chain constant region fusion protein and DNA sequence are shown in SEQ ID NOs: 21 and 22, the mature polypeptide sequence of which is SEQ ID NO: 41.

The IL-20RA extracellular domain human immunoglobulin gamma 1 heavy constant region fusion protein and DNA sequence are shown in SEQ ID NOs: 23 and 24, the mature polypeptide sequence of which is SEQ ID NO: 39.

EXAMPLE 4

Construction of an IL-20 Receptor Heterodimer

A vector expressing a secreted hIL-20RA/hIL-20B heterodimer was constructed. In this construct, the extracellular domain of hIL-20RA was fused to the heavy chain of IgG gamma 1 (IgGγ1), while the extracellular portion of IL-20RB was fused to human kappa light chain (human κ light chain).

Construction of IgG Gamma 1 and Human κ Light Fusion Vectors

The heavy chain of IgGγ1 was cloned into the Zem229R mammalian expression vector (ATCC deposit No. 69447) such that any extracellular portion of a receptor having a 5' EcoRI and 3' NheI site can be cloned in, resulting in an N-terminal extracellular domain-C-terminal IgGγ1 fusion. The IgGγ1 fragment used in this construct was made by using PCR to isolate the IgGγ1 sequence from a Clontech hFetal Liver cDNA library as template. A PCR reaction using oligos (SEQ ID NO: 25) ZC11,450 and (SEQ ID NO: 26) ZC11,443 was run as follows: 40 cycles of 94° for 60 sec., 53° C. for 60 sec., and 72° for 120 sec.; and 72° C. for 7 min. PCR products were separated by agarose gel electrophoresis and purified using a QiaQuick™ (Qiagen) gel extraction kit. The isolated, 990 bp, DNA fragment was digested with MluI and EcoRI (Boerhinger-Mannheim), ethanol precipitated and ligated with oligos (SEQ ID NO: 27) ZC11,440 and (SEQ ID NO: 28) ZC11,441, which comprise an MluI/EcoRI linker, into Zem229R previously digested with MluI and EcoRI using standard molecular biology techniques disclosed herein. This generic cloning vector was called Vector#76 hIgGgamma1 w/Ch1 #786 Zem229R (Vector #76). The polynucleotide sequence of the extracellular domain of hIL-20RA fused to the heavy chain of IgG gamma 1 is show in SEQ ID NO: 29 and the corresponding polypeptide sequence shown in SEQ ID NO: 30, the mature sequence of which is SEQ ID NO: 40.

The human κ light chain was cloned in the Zem228R mammalian expression vector (ATCC deposit No. 69446) such that any extracellular portion of a receptor having a 5' EcoRI site and a 3' KpnI site can be cloned in, resulting in an N-terminal terminal extracellular domain-C-terminal human κ light chain fusion. The human κ light chain fragment used in this construct was made by using PCR to isolate the human κ light chain sequence from the same Clontech hFetal Liver cDNA library used above. A PCR reaction using oligos (SEQ ID NO: 31) ZC11,501 and (SEQ ID NO: 32) ZC11,451 was run under condition described above. PCR products were separated by agarose gel electrophoresis and purified using a QiaQuick™ (Qiagen) gel extraction kit. The isolated, 315 bp, DNA fragment was digested with MluI and EcoRI (Boerhinger-Mannheim) ethanol precipitated and ligated with the MluI/EcoRI linker described above, into Zem228R previously digested with MluI and EcoRI using standard molecular biology techniques disclosed herein. This generic cloning vector was called Vector #77 hκlight #774 Zem228R (Vector #77). The polynucleotide sequence of the extracellular portion of IL-20RB fused to human kappa light chain is shown in SEQ ID NO: 33 and the corresponding polypeptide sequence shown in SEQ ID NO: 34, the mature sequence of which is SEQ ID NO: 42.

Insertion of hIL-20RA and IL-20RB Extracellular Domains into Fusion Vector Constructs Using the construction vectors above, a construct having human IL-20RA fused to IgGγ1 was made. This construction was done by PCRing human IL-20RA receptor from hIL-20RA/IgG Vector #102 with oligos (SEQ ID NO: 35) ZC12,909 and (SEQ ID NO: 36) ZC26,564 under conditions described as follows: 30 cycles of 94° C. for 60 sec., 57° C. for 60 sec., and 72° C. for 120 sec.; and 72° C. for 7 min. The resulting PCR product was digested with EcoRI and NheI, gel purified, as described herein, and ligated into a previously EcoRI and NheI digested and band-purified Vector #76 (above). The resulting vector was sequenced to confirm that the human IL-20Rα/IgG gamma 1 fusion (hIL-20RA/Ch1 IgG) was correct. The hIL-20RA /Ch1 IgG gamma 1 #1825 Zem229R vector was called vector #195.

A separate construct having IL-20RB fused to κ light was also constructed. The IL-20RB/human κ light chain construction was performed as above by PCRing from DR1/7N-4 with oligos (SEQ ID NO: 37) ZC26,602 and (SEQ ID NO: 38) ZC26,599, digesting the resulting band with EcoRI and KpnI and then ligating this product into a previously EcoRI and KpnI digested and band-purified Vec#77 (above). The resulting vector was sequenced to confirm that the IL-20RB/human κ light chain fusion (IL-20RB/κlight) was correct. This IL-20RB//κlight #1833 Zem228R vector was called Vector #194.

Co-expression of the Human IL-20RA and Human IL-20RB Receptors

Approximately 16 μg of each of vectors #194 and #195, above, were co-transfected into BHK-570 cells (ATCC No. CRL-10314) using LipofectaminePlus™ reagent (Gibco/BRL), as per manufacturer's instructions. The transfected cells were selected for 10 days in DMEM+5%FBS (Gibco/BRL) containing 1 μM of methotrexate (MTX) (Sigma, St. Louis, Mo.) and 0.5 mg/ml G418 (Gibco/BRL) for 10 days. The resulting pool of tranfectants was selected again in 10 μM MTX and 0.5 mg/ml G418 for 10 days.

The resulting pool of doubly selected cells was used to generate protein. Three factories (Nunc, Denmark) of this pool were used to generate 8 L of serum free conditioned medium. This conditioned media was passed over a 1 ml protein-A column and eluted in (10) 750 microliter fractions. 4 of these fractions found to have the highest concentration were pooled and dialyzed (10 kD MW cutoff) against PBS. Finally, the dialyzed material was analyzed by BCA (Pierce) and found to have a concentration of 317 μg/ml. A total of 951 μg was obtained from this 8 L purification.

EXAMPLE 5

Proliferation Assay on Baf3/IL-20RA/IL-20RB Stable Cell Lines

Object of the Example

The object of the present example was to determine if IL-19 could bind to cell lines that express the IL20RA/IL-20RB heterodimeric receptor.

IL-19 was placed in a dose response proliferation assay in Baf3/IL-20RA/IL-20RB Stable Cell Lines. The proliferation assay was set up as follows:

Day 1: A 96-well plate at 5000 cells/well was seeded with a dose response of IL-19 from 6 ng/ml down to 0.01 ng/ml and controls, and the cells were incubated at 37° C.

Day 4: 20 μl of Alamar Blue were placed in each well and let the cells were incubated at 37° C. overnight.

Day 5: The plate on the plate reader in robotics in Fluoresces Units (544 nm ex./590 nm em.). The data are shown below.

Results: The data below are the number of cells in each well and indicates that the cells proliferated in a dose-dependent response to IL-19.

TABLE 1

|  | Basal | 0.01 ng/ml | 0.02 ng/ml | 0.05 ng/ml | 0.09 ng/ml | 0.19 ng/ml |
|---|---|---|---|---|---|---|
| IL-19 (A096G) | 351 | 952 | 1463 | 2415 | 3406 | 4110 |
|  | 15.76368 | 114.4513 | 156.6867 | 265.7708 | 122.874 | 33.92484 |
|  | 15.76 | 59.29149 | 93.94366 | 74.18359 | 144.9331 | 136.9183 |

TABLE 1-continued

|  | 0.38 ng/ml | 0.75 ng/ml | 1.5 ng/ml | 3 ng/ml | 6 ng/ml |
|---|---|---|---|---|---|
| IL-19 (A096G) | 4528 | 4962 | 5194 | 5499 | 5664 |
|  | 172.5072 | 185.7348 | 177.8779 | 92.49958 | 83.41251 |
|  | 84.89956 | 49.76869 | 83.2038 | 49.12525 | 43.42404 |

TABLE 2

|  | 1 | 2 | 3 | 4 | 5 | 6 | 7 | 8 | 9 | 10 | 11 | 12 |
|---|---|---|---|---|---|---|---|---|---|---|---|---|
| A | 6528.9 | 5722.8 | 5619.8 | 5492.3 | 5338.3 | 4896.2 | 4285.9 | 3621 | 3563.9 | 2104 | 1443.5 | 373.79 |
| B | 6544.8 | 5540.1 | 5421.6 | 5133.1 | 4976.4 | 4676.9 | 4376.6 | 3933.5 | 3240.5 | 2221.8 | 1149.4 | 351.74 |
| C | 6554.7 | 5541.9 | 5402.7 | 5160.9 | 4981.9 | 4646.2 | 4325.9 | 3908.5 | 3029.9 | 2071.4 | 1181 | 321.27 |
| D | 6457.9 | 5689.5 | 5397.3 | 5012.6 | 4835.6 | 4409.4 | 4304.4 | 3831.3 | 2849.4 | 1794.4 | 1276.7 | 368.39 |
| E | 6537.7 | 5627.4 | 5496.6 | 5304 | 4962.9 | 4622 | 4341.3 | 3573.1 | 2521.7 | 1390.6 | 921.81 | 340.1 |
| F | 6494.5 | 5708 | 5532.4 | 5235.2 | 4880.5 | 4603.9 | 4055.3 | 3433.2 | 2416.2 | 1423.1 | 872.13 | 341.37 |
| G | 6492.6 | 5613.8 | 5419.6 | 5082.8 | 5002 | 4445.3 | 4061.1 | 3173.9 | 2312.1 | 1413.5 | 989.98 | 352.52 |
| H | 6562.8 | 5705.8 | 5546.2 | 5154.9 | 5002.8 | 4442 | 3983.1 | 3444.6 | 2408.8 | 1624.3 | 1025 | 359.24 |

EXAMPLE 6

Neutralization Assay of IL-19

Object of the Example

The object of the present example was to determine if the soluble IL-20RA/IL-20RB heterodimeric receptor could neutralize IL-19.

Day 1: Baby hamster kidney (BHK) cells expressing the IL-20RA/IL-20RB heterodimeric receptor were plated at 1000 cells/well in a 96 well plate.

Day 2: The cells were re-plated into serum-free medium to down regulate their response.

Day 3: Three different solutions containing IL-19 were made, one having a concentration of 0.1 ng/ml, the second solution having a concentration of 1 ng/ml and the third having a concentration of 10 ng/ml.

As a control experiment, 100 µl aliquots of each of the solutions of IL-19 were placed in different cell-containing wells to determine the level of proliferation of the cells caused by IL-19.

In a second experiment, 100 µl of a solution containing the soluble IL-20A/IL-20B heterodimeric receptor having a concentration of 10 µg/ml were mixed with 100 µl aliquots of each of the solutions of IL-19 and vortexed to thoroughly mix the solutions. The solutions were then let to sit at room temperature for 30 minutes. The mixed solutions were then loaded in triplicate in the wells containing the BHK cells that express the IL-20RA/IL-20RB receptors. The microtiter plates containing the cells were then incubated at 37° C. for 4 hours, then read on a luminometer and the data collected.

The data in the tables below indicate the number of cells present at the end of the experiment. As can be see the soluble receptor neutralized some of IL-19's activity at all three concentrations (especially the higher concentration) when compared to IL-19's activity alone.

TABLE 3

|  | Basal | 0.1 ng/ml | 1 ng/ml | 10 ng/ml |
|---|---|---|---|---|
| zmda1 Alone | 3370 | 11488 | 18684 | 25148.33 |
| Soluble Receptor (A442F) 10 µg/ml | 80.06664 | 282.8722 | 223.1457 | 770.5052 |

TABLE 4

|  | Basal | 0.1 ng/ml | 1 ng/ml | 10 ng/ml |
|---|---|---|---|---|
| Soluble Receptor (A442F) 10 µg/ml + Zmda1 | 3574.667 105.3291 | 6115.333 435.0788 | 13160.67 672.2645 | 20687 582.3624 |

What is claimed is:

1. A method down-regulating IL-19 comprising administering to an individual a polypeptide comprising the extracellular domain of IL-20RA and the extracellular domain of IL-20RB, wherein the extracellular domain of IL-20RA comprises SEQ ID NO:3 and the extracellular domain of IL-20RB comprises SEQ ID NO:6.

* * * * *